(12) United States Patent
Justis et al.

(10) Patent No.: US 8,607,603 B2
(45) Date of Patent: Dec. 17, 2013

(54) SYSTEMS, DEVICES AND METHODS FOR MULTI-DIMENSIONAL BENDING OF AN ELONGATE MEMBER

(75) Inventors: Jeff R Justis, Germantown, TN (US); Hai H Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 558 days.

(21) Appl. No.: 12/770,980

(22) Filed: Apr. 30, 2010

(65) Prior Publication Data
US 2011/0265538 A1   Nov. 3, 2011

(51) Int. Cl.
*B21D 11/00*   (2006.01)

(52) U.S. Cl.
USPC ............ 72/31.04; 72/31.05; 72/306; 72/307; 72/380; 72/381; 72/384; 72/394; 72/403; 72/342.1; 72/342.94; 72/16.5; 72/18.3; 72/19.1; 140/123

(58) Field of Classification Search
USPC ............ 72/31.04, 31.05, 306, 307, 380, 381, 72/384, 394, 403, 342.1, 342.94, 16.5, 72/18.3, 19.1; 140/123
See application file for complete search history.

(56) References Cited

U.S. PATENT DOCUMENTS

| | | | |
|---|---|---|---|
| 3,866,458 A * | 2/1975 | Wagner | 72/459 |
| 4,474,046 A | 10/1984 | Cook | |
| 4,827,753 A * | 5/1989 | Moroney | 72/296 |
| 5,113,685 A | 5/1992 | Asher et al. | |
| 5,161,404 A | 11/1992 | Hayes | |
| 5,290,281 A | 3/1994 | Tschakaloff | |
| 5,345,799 A * | 9/1994 | Miodushevski et al. | 72/19.8 |
| 5,389,099 A | 2/1995 | Hartmeister et al. | |
| 5,490,409 A | 2/1996 | Weber | |
| 5,548,985 A | 8/1996 | Yapp | |
| 5,564,302 A | 10/1996 | Watrous | |
| 5,591,165 A | 1/1997 | Jackson | |
| 5,651,283 A | 7/1997 | Runciman | |
| 5,658,286 A | 8/1997 | Sava | |
| 5,819,580 A | 10/1998 | Gauthier | |
| 5,938,662 A | 8/1999 | Rinner | |
| 6,006,581 A | 12/1999 | Holmes | |
| 6,035,691 A * | 3/2000 | Lin et al. | 72/413 |
| 6,077,271 A | 6/2000 | Huebner | |
| 6,128,944 A | 10/2000 | Haynes | |
| 6,221,077 B1 | 4/2001 | Rinner et al. | |
| 6,332,780 B1 | 12/2001 | Traxel et al. | |
| 6,612,143 B1 | 9/2003 | Butscher et al. | |
| 6,644,087 B1 * | 11/2003 | Ralph et al. | 72/213 |

(Continued)

FOREIGN PATENT DOCUMENTS

GB   2 267 757   12/1993

*Primary Examiner* — Dana Ross
*Assistant Examiner* — Onekki Jolly

(57) ABSTRACT

Systems, devices and methods are provided for bending an elongate member used in association with a medical procedure. In one form, a device for bending an elongate member includes a support platform and a plurality of engaging members positioned on the support platform. Each of the plurality of engaging members includes at least one engaging portion configured for positioning in contact with the elongate member. Each of the plurality of engaging members is movable in at least three directions relative to the support platform to form one or more bends in the elongate member. In one aspect, the elongate member is formed of a heat deformable material and the device includes a heating member configured to apply heat to one or more portions of the elongate member to facilitate bending. However, other embodiments, forms and applications are also envisioned.

12 Claims, 10 Drawing Sheets

(56) References Cited

U.S. PATENT DOCUMENTS

| | | |
|---|---|---|
| 6,978,188 B1 | 12/2005 | Christensen |
| 7,115,129 B2 | 10/2006 | Heggeness |
| 2003/0055435 A1 | 3/2003 | Barrick |
| 2004/0144149 A1 | 7/2004 | Strippgen et al. |
| 2005/0262911 A1 | 12/2005 | Dankowicz et al. |
| 2006/0150699 A1* | 7/2006 | Garner et al. .............. 72/31.04 |
| 2006/0235427 A1 | 10/2006 | Thomas et al. |
| 2006/0264934 A1 | 11/2006 | Fallin |
| 2006/0264973 A1 | 11/2006 | Abdelgany |
| 2007/0093824 A1 | 4/2007 | Hestad et al. |
| 2007/0227216 A1 | 10/2007 | Schalliol |
| 2007/0233079 A1 | 10/2007 | Fallin et al. |
| 2007/0233111 A1 | 10/2007 | Orbay et al. |
| 2008/0086127 A1 | 4/2008 | Patterson et al. |
| 2008/0125817 A1 | 5/2008 | Arnett et al. |

\* cited by examiner

SYSTEMS, DEVICES AND METHODS FOR MULTI-DIMENSIONAL BENDING OF AN ELONGATE MEMBER

CROSS-REFERENCE TO RELATED APPLICATIONS

This application is related to a co-pending U.S. patent application entitled "SYSTEMS, DEVICES AND METHODS FOR BENDING AN ELONGATE MEMBER" filed on the same day as the subject application, the contents of which are hereby incorporated by reference in their entirety.

BACKGROUND

The present invention generally relates to systems, devices and methods for bending an elongate member used in association with a medical procedure. In one form, the medical procedure is a spinal stabilization procedure wherein an orthopedic construct is engaged along the spinal column, and the elongate member is a rod component anchored to the spinal column by a number of bone anchors.

The use of spinal constructs to stabilize and support a portion of the spinal column has become commonplace. In particular, spinal constructs frequently include several bone anchors that are anchored to various portions of the spinal column, and an elongate rod that extends between and is engaged with the bone anchors to provide stabilization and support to the spinal column. Typically, the elongate rod is initially provided in a substantially straight configuration, and is subsequently bent or contoured to facilitate engagement with each of the bone anchors and/or to provide a desired spinal curvature.

Prior techniques and instrumentation for bending elongate rods can have limited applications in providing elongate rods with complex or compound curvatures. Additionally, prior techniques and instrumentation for bending elongate rods require application of excessive bending forces, and thereby risk fracturing or degradation of the elongate rod and/or degrading the material properties associated with the elongate rod. In this arena, the desire persists for improved rod bending/contouring capabilities. Thus, there is a need for additional contributions in this area of technology.

SUMMARY

One non-limiting embodiment of the present invention is directed to a device for bending an elongate member used in association with a medical procedure. In one form of the present invention, the medical procedure is a spinal stabilization procedure, and the elongate member is a rod component anchored to the spinal column by a number of bone anchors. However, bending of other types of elongate members is also contemplated by the present invention. Additionally, the elongate member may be formed of a heat deformable material which softens or becomes less rigid as it is heated to provide increased flexibility to facilitate bending/contouring of the elongate member, although embodiments in which the elongate member is not formed of a heat deformable material are also contemplated.

In another embodiment, a device for bending an elongate member used in a medical procedure includes a support platform and a plurality of engaging members positioned on the support platform. Each of the plurality of engaging members includes an engaging portion configured for positioning in contact with the elongate member and is movable in at least three directions relative to the support platform to form one or more bends in the elongate member. In one form of this embodiment, the device also includes a heating member structured and arranged to apply heat to select portions of the elongate member to facilitate bending of the select portions by the plurality of engaging members to form one or more bends in the elongate member.

In yet another embodiment, a system for bending an elongate rod used in a medical procedure includes a bending device including a support platform and a plurality of engaging members movable relative to the support platform. The engaging members include a first set of engaging portions positioned on a first side of a horizontal member of the support platform, and a second set of engaging portions positioned on a second side of the horizontal member of the support platform. The system also includes an elongate template member including a contoured configuration positionable in the first set of engaging portions, and an elongate spinal rod positionable in the second set of engaging portions. When the elongate template member is positioned in the first set of engaging members, the engaging members of the first set of engaging members are arranged in a first orientation that corresponds to the contoured configuration of the template member, and the engaging members of the second set of engaging members are arranged in a second orientation that corresponds to the first orientation in order to form one or more bends in the elongate spinal rod and provide the elongate spinal rod with a contoured configuration that mirrors the contoured configuration of the elongate template member. In one form of this embodiment, the elongate spinal rod is formed of a heat deformable material, and the bending device further includes a heating member configured to apply heat to one or more portions of the elongate spinal rod when the elongate spinal rod is positioned in the second set of engaging portions in order to facilitate bending of the elongate spinal rod.

In a further embodiment, a method for bending an elongate support member associated with an orthopedic construct includes providing a bending device including a support platform and a plurality of engaging members positioned on the support platform. Each of the plurality of engaging members includes at least one engaging portion, and is movable in at least three directions relative to the support platform to form one or more bends in the elongate support member. The method further includes positioning an elongate template member including a contoured configuration in at least a portion of the engaging portions of the plurality of engaging members, and bending the elongate support member to include a contoured configuration that substantially corresponds to the contoured configuration of the elongate template member.

Another embodiment of the invention is directed to a unique system and method for bending a rod component used in association with a spinal implant construct. Other embodiments include unique methods, systems, devices, kits, assemblies, equipment, and/or apparatuses directed to forming or contouring an elongate rod component with one or more simple or complex or compound bends.

Further embodiments, forms, features, aspects, benefits, objects and advantages of the present invention will become apparent from the detailed description and figures provided herewith.

DESCRIPTION OF THE ILLUSTRATED EMBODIMENTS

Figure 1:
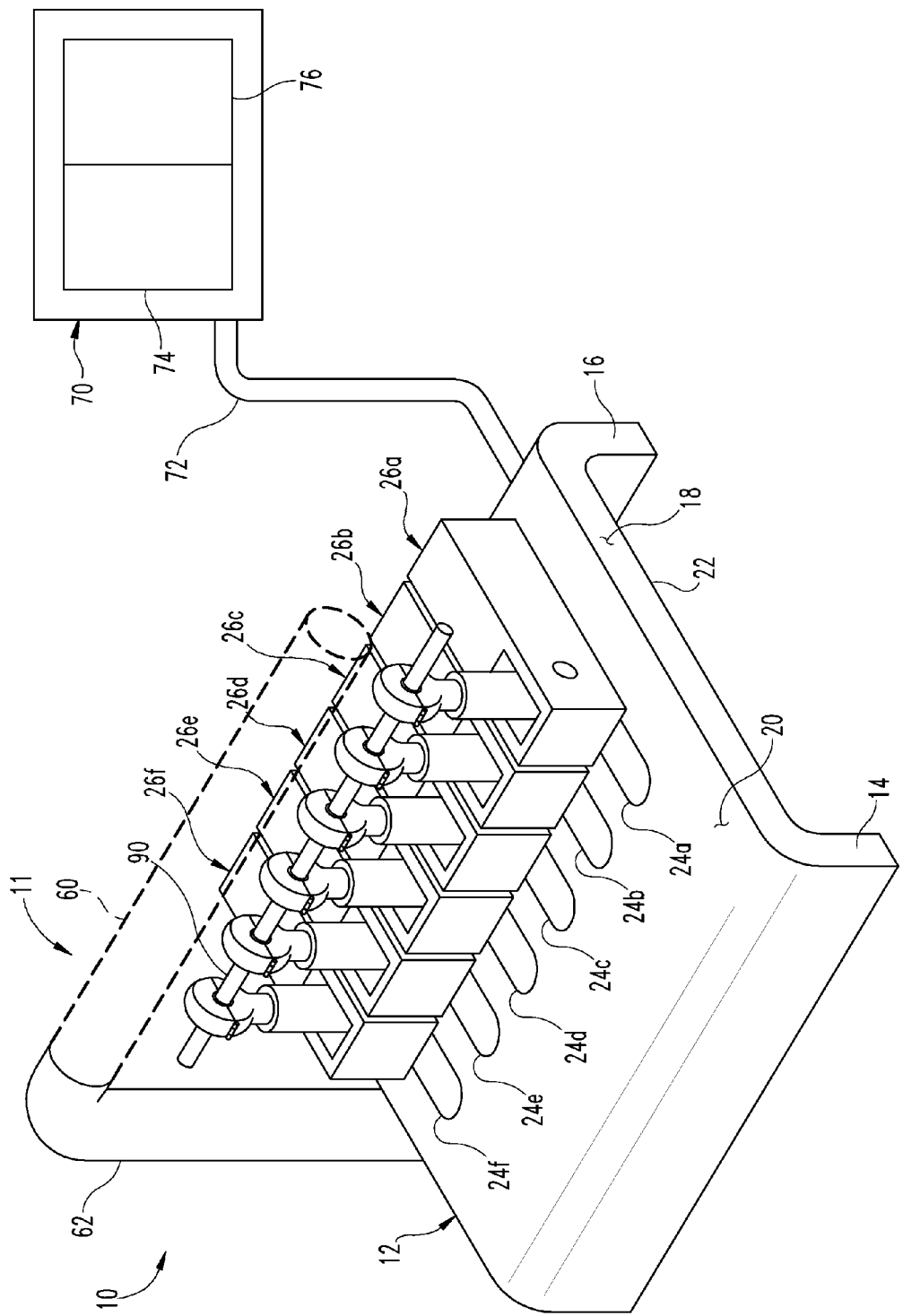
FIG. 1 is a perspective view of one embodiment of a rod bending device.

For the purposes of promoting an understanding of the principles of the invention, reference will now be made to the embodiments illustrated in the drawings and specific language will be used to describe the same. It will nevertheless be understood that no limitation on the scope of the invention is hereby intended. Any alterations and further modifications in the illustrated devices and described methods and further applications of the principles of the invention as disclosed herein are contemplated as would normally occur to one skilled in the art to which the invention relates.

Systems, devices and methods for bending or contouring an elongate member used in association with a medical procedure are provided. In one form, the medical procedure is a spinal stabilization procedure wherein a spinal construct is engaged along the spinal column. In a further form, the elongate member is a rod component anchored to the spinal column by a number of bone anchors to provide stabilization and support to the spinal column. However, other types of elongate members are also contemplated for use in association with the present invention, including plate components or other suitable types of elongate support components. In one embodiment, the bone anchors are initially anchored to portions of the spinal column, followed by engagement of the rod component to the bone anchors. The rod component may require bending or contouring to allow for interconnection with the bone anchors and/or to provide a desired spinal curvature. The spinal construct may be used in association with, but is not limited to, treatment of degenerative spondylolisthesis, fracture, dislocation, scoliosis, kyphosis, or spinal tumors.

Referring now to FIG. 1, illustrated therein is a device 10 according to one form of the present invention for bending or contouring an elongate rod member 90. As indicated above, other types of elongate members are also contemplated for use in association with the present invention, including plate components or other suitable types of elongate support components. The device 10 includes a bending mechanism 11 operably coupled with a user interface 70 via a pathway 72. Further details regarding the user interface 70 will be set forth below. However, it should be appreciated that in other embodiments, the device 10 need not be provided with the user interface 70. The bending mechanism 11 is structured to bend or contour the elongate rod member 90 at one or more axial locations along the length of the elongate rod member 90. The bending mechanism 11 includes a support platform 12 having a first vertical leg 14 and a second vertical leg 16 that each extend from a horizontal member 18. The horizontal member 18 includes an upper surface 20 positioned opposite a lower surface 22. However, it should be appreciated that the illustrated configuration of the support platform 12 is exemplary, and that support platforms having other sizes, shapes and configurations are also contemplated for use in association with the present invention. The horizontal member 18 also includes a plurality of elongated slots 24a-24f that extend through the horizontal member between the upper and lower surfaces 20 and 22. The bending mechanism 11 further includes a plurality of engaging members 26a-26f correspondingly positioned adjacent the elongated slots 24a-24f, respectively. Each of the engaging members 26a-26f is movable in a plurality of directions relative to the support platform 12, further details of which will be provided below in connection with the engaging member 26a. However, it should be appreciated that the details provided with regard to the engaging member 26a are also applicable to the other engaging members 26b-26f.

Figure 2:
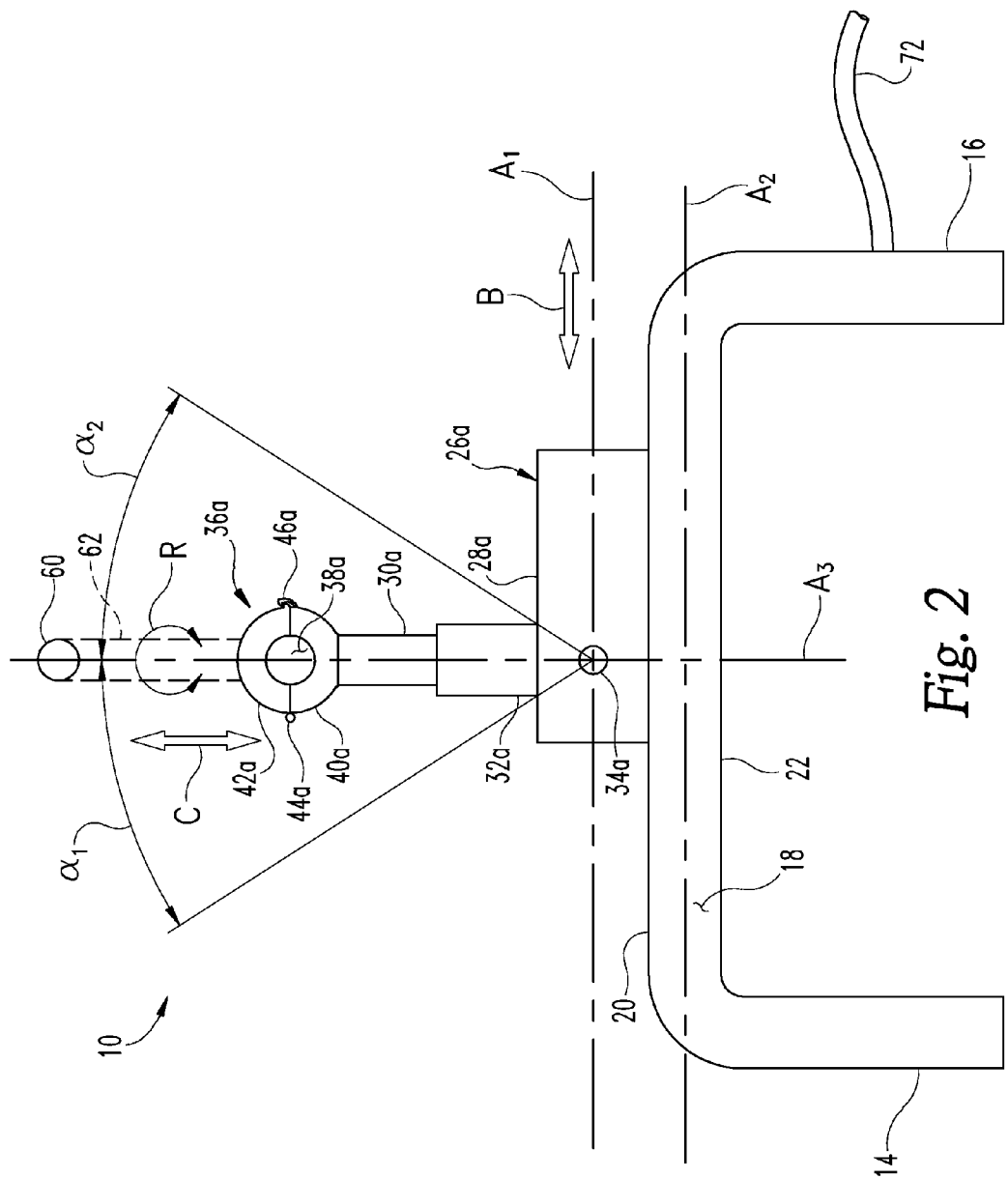
FIG. 2 is an end view of the rod bending device illustrated in FIG. 1.

As shown in the end view of the device 10 in FIG. 2, the elongate rod member 90 has been omitted for the sake of clarity. The engaging member 26a includes a base member 28a that extends generally along an axis $A_1$ that is substantially parallel to or inline with axis $A_2$ along which the horizontal member 18 extends, although forms where the axis $A_1$ and the axis $A_2$ are oriented in different arrangements are also contemplated. The base member 28a is coupled to the horizontal member 18 and is arranged relative to the elongated slot 24a in the horizontal member 18 such that it is slidable to any number of positions along the length of the elongated slot 24a relative to the horizontal member 18, as indicated by directional arrow B. It should be appreciated that various arrangements may be utilized to displace the engaging member 26a along the elongated slot 24a to select positions relative to the other engaging members 26b-26f and relative to the support platform 12. For example, in one embodiment, the engaging member 26a may be coupled to and movable by a rack and pinion mounting structure. The rack and pinion structure may include a rack portion coupled to the engaging member 26a and a pinion portion coupled to the support platform 12. However, a reverse configuration is also contemplated wherein the rack portion is coupled to the support platform 12 and the pinion portion is coupled to the engaging member 26a. Each pinion portion includes a pinion gear that engages teeth formed along the rack portion. Rotation of the pinion gear displaces the engaging member 26a to position the engaging member 26a along the length of the slot 24a and at a select location relative to the support platform 12. The pinion gear may be driven by various types of drives or actuators including, for example, an electric or pneumatic motor. In other embodiments, linear actuators or drives including, for example, pneumatic cylinders or electric screws, may be utilized to selectively position the engaging member 26a relative to the other engaging members 26b-26f and relative to the support platform 12. Still, further embodiments for facilitating selective positioning of the engaging member 26a along the axis $A_1$ include ball-detent mechanisms and releasably interlocking cams or tabs, just to name a few other possibilities.

The engaging member 26a also includes an elongate member 30a that is positioned in and coupled with a sleeve member 32a, which is in turn pivotably coupled with the base member 28a via a pivot pin 34a, although other forms where the sleeve member 32a is not pivotably coupled to the base member 28a are also contemplated. The elongate member 30a extends along an axis $A_3$ that extends transversely to the axes $A_1$ and $A_2$. In this arrangement, the elongate member 30a is pivotally movable relative to the base member 28a, as well as the support platform 12, as the sleeve member 32a is pivoted relative to the base member 28a. In one form, the sleeve member 32a may be pivoted up to thirty degrees in opposite lateral directions as indicated by angles $\alpha_1$ and $\alpha_2$. However, it should be appreciated that alternative angles $\alpha_1$ and $\alpha_2$ are also contemplated. Various arrangements for pivoting the sleeve member 32a relative to the base member 28a are contemplated. For example, in one form, one or more rotary actuators or drives may be utilized to rotate and maintain positioning of the sleeve member 32a relative to the base member 28a. In another form, it is contemplated that the sleeve member 32a may be manually pivoted relative to the base member 28a, and the base member 28a may be provided with a locking member, such as a set screw, that may be selectively engaged with the sleeve member 32a to lock the relative positioning of the sleeve member 32a and the base member 28a.

The elongate member 30a is also axially translatable relative to the sleeve member 32a and the base member 28a along the axis $A_3$, as indicated by directional arrow C. Various arrangements for axially translating the elongate member 30a relative to the sleeve member 32a and the base member 28a are contemplated. For example, in one form, one or more linear actuators or drives may be utilized to axially translate and maintain positioning of the elongate member 30a relative to the sleeve member 32a and the base member 28a. In another form, it is contemplated that a rack and pinion arrangement may be disposed between the elongate member 30a and the sleeve member 32a in order to facilitate axial translation and positioning of the elongate member 30a at any of a number of positions along the axis $A_3$. However, it should also be appreciated that in another form, the elongate member 30a may be manually axially-translated relative to the sleeve member 32a and the base member 28a, and the sleeve member 32a may be provided with a locking member, such as a set screw, that may be selectively engaged with the elongate member 30a in order to lock the axial positioning of the elongate member 30a relative to the sleeve member 32a and the base member 28a.

In addition to the foregoing, the elongate member 30a is also mounted relative to the base member 28a in a manner which allows the elongate member 30a to rotate about axis $A_3$ relative to the sleeve member 32a and the base member 28a in the direction of arrows R. Various arrangements for rotating the elongate member 30a relative to the sleeve member 32a and the base member 28a are contemplated. For example, in one form, one or more rotary actuators or drives may be utilized to rotate and maintain positioning of the elongate member 30a relative to the sleeve member 32a and the base member 28a. In another form, it is contemplated that the elongate member 30a may be manually rotated relative to the sleeve member 32a and the base member 28a, and the sleeve member 32a may be provided with a locking member, such as a set screw, that may be selectively engaged with the elongate member 30a in order to lock the relative positioning of the elongate member 30a and the sleeve member 32a.

The elongate member 30a also includes an engaging portion 36a that includes a circular-shaped opening 38a within which the elongate rod member 90 may be positioned. In the form illustrated in FIG. 2, the engaging portion 36a includes a pair of rod engaging elements 40a, 42a that are pivotally coupled to one another via a pivot or hinge element 44a. The rod engaging elements 40a, 42a may be maintained in a closed or captured position via a latch or lock element 46a. As should be appreciated, the elongate rod member 90 is engaged with the engaging portion 36a by pivoting the rod engaging element 42a to an open position and laterally loading the elongate rod member 90 into half of the circular-shaped opening 38a defined by the rod engaging element 40a, followed by pivoting the rod engaging element 42a about the pivot element 44a to a closed position to capture the elongate rod member 90 within the circular-shaped opening 38a, and maintaining the rod engaging elements 40a, 42a in the closed or captured position via the latch element 46a.

As indicated above, in the form illustrated in FIG. 2, the opening 38a includes a circular shape. However, it should be appreciated that alternative configurations for the opening 38a are also contemplated. For example, in other embodiments, the opening 38a of the engaging portion 36a may be provided with a polygonal, oval, or elliptical shape/configuration, or any other suitable shape/configuration that would occur to one of ordinary skill in the art. It should be understood that the opening 38a of the engaging portion 36a, regardless of its shape and configuration, may be provided with a convexly-curved bottom surface having a saddle-like configuration to facilitate pivotal movement of the elongate rod member 90 relative to the opening 38a. Additionally, in one embodiment, the opening 38a of the engaging portion 36a is provided with a smooth surface finish to avoid scratching, gouging or otherwise damaging the outer surface of the elongate rod member 90. However, in other embodiments, the opening 38a of the engaging portion 36a may be somewhat roughened and/or provided with one or more gripping elements to facilitate secure engagement with elongate the rod member 90.

In view of the foregoing, it should be appreciated that each of engaging members 26a-26f is movable in a plurality of directions relative to the support platform 12 and to one another in order to bend the elongate rod member 90 to a desired shape/contour, further details of which will be provided below. When the elongate rod member 90 is positioned in the engaging portions of the engaging members 26a-26f, relative movement of the engaging members 26a-26f compressively engages the engaging members 26a-26f against the elongate rod member 90 to thereby bend the elongate rod member 90 to a desired contour or curvature along one or more portions of the rod length. As should be appreciated, the contour or curvature of the elongate rod member 90 is dictated or governed by the particular position and orientation of the individual engaging members 26a-26f relative to one another and relative to the elongate rod member 90. In one particular form, the device 10 may be provided with one or more sensors that may sense and record the relative positioning of each of the engaging members 26a-26f in a select orientation, further details of which will be discussed below.

As illustrated in FIGS. 1 and 2, the device 10 further includes a heating mechanism or element 60 (shown in dashed lines in FIG. 1 for purposes of clarity) positioned above the engaging members 26a-26f and the support platform 12. However, it should be appreciated that in alternative forms, the heating element 60 may be omitted from the device 10. As illustrated in FIG. 1, a support member 62 extends from an end of the horizontal member 18 and is coupled to the heating element 60 to mount the heating element 60 in a select position and orientation relative to the engaging members 26a-26f. In the illustrated embodiment of the device 10, the heating element 60 is generally centered over the engaging members 26a-26f. In this arrangement, the heating element 60 provides a relatively uniform application of heat to the elongate rod member 90 when the elongate rod member 90 is positioned in the engaging portions of the engaging members 26a-26f. However, in other non-illustrated embodiments, the support member 62 may be adjustable to facilitate adjustable positioning of the heating element 60 toward or away from the elongate rod member 90. In one alternative embodiment, the support member 62 may be formed of a multi-directional flexible material to allow adjustable positioning of the heating element 60 in a plurality of positions and orientations relative to the elongate rod member 90 when positioned in the engaging portions of the engaging members 26a-26f. Additionally, in the illustrated embodiment, the heating element 60 is configured to apply heat to substantially the entire length of the elongate rod member 90. However, in other embodiments, the heating element 60 may be configured to apply heat to select axial portions of the elongate rod member 90 such as, for example, to the particular portions of the elongate rod member 90 to be bent by the bending mechanism 11. Furthermore, although the heating element 60 is illustrated as a single element having a linear configuration, it should be understood that the heating element 60 may be comprised of multiple segments/elements and/or may be provided with a curved configuration, a curvilinear configuration, an angled configuration, or any other suitable configuration.

The heating element 60 is generally structured to apply heat to one or more portions of the elongate rod member 90, or the entire length of the elongate rod member 90, when positioned in the engaging portions of the engaging members 26a-26f. The heating element 60 may take any form or configuration suitable to apply heat to the elongate rod member 90. For example, the heating element 60 may be configured to provide heat via convection heating, conduction heating, infrared heating, or any other type of heating known to those of skill in the art. Additionally, the heating element 60 may utilize power from an internal or external power source to provide heat in a variety of manners including, for example, via a coil resistance heater, a metal oxide resistance heater, or a PTC (Positive Temperature Coefficient) heater, just to name a few possibilities. In one particular embodiment, the heating element 60 comprises an infrared heating element. In other embodiments, the heating element 60 comprises a band heater and/or a cartridge heater. In still other embodiments, the heating element 60 directs hot air toward the elongate rod member 90. Other suitable arrangements or configurations of the heating elements 60 are contemplated in addition to or in lieu of those specifically described above. Furthermore, in addition to applying heat to the elongate rod member 90, the heating element 60 may also be configured to control or regulate the temperature of the elongate rod member 90 via various cooling or refrigeration systems including, for example, convection cooling by way of air, water or other convective media and/or conductive cooling systems, further details of which will be set forth below.

Figure 3:
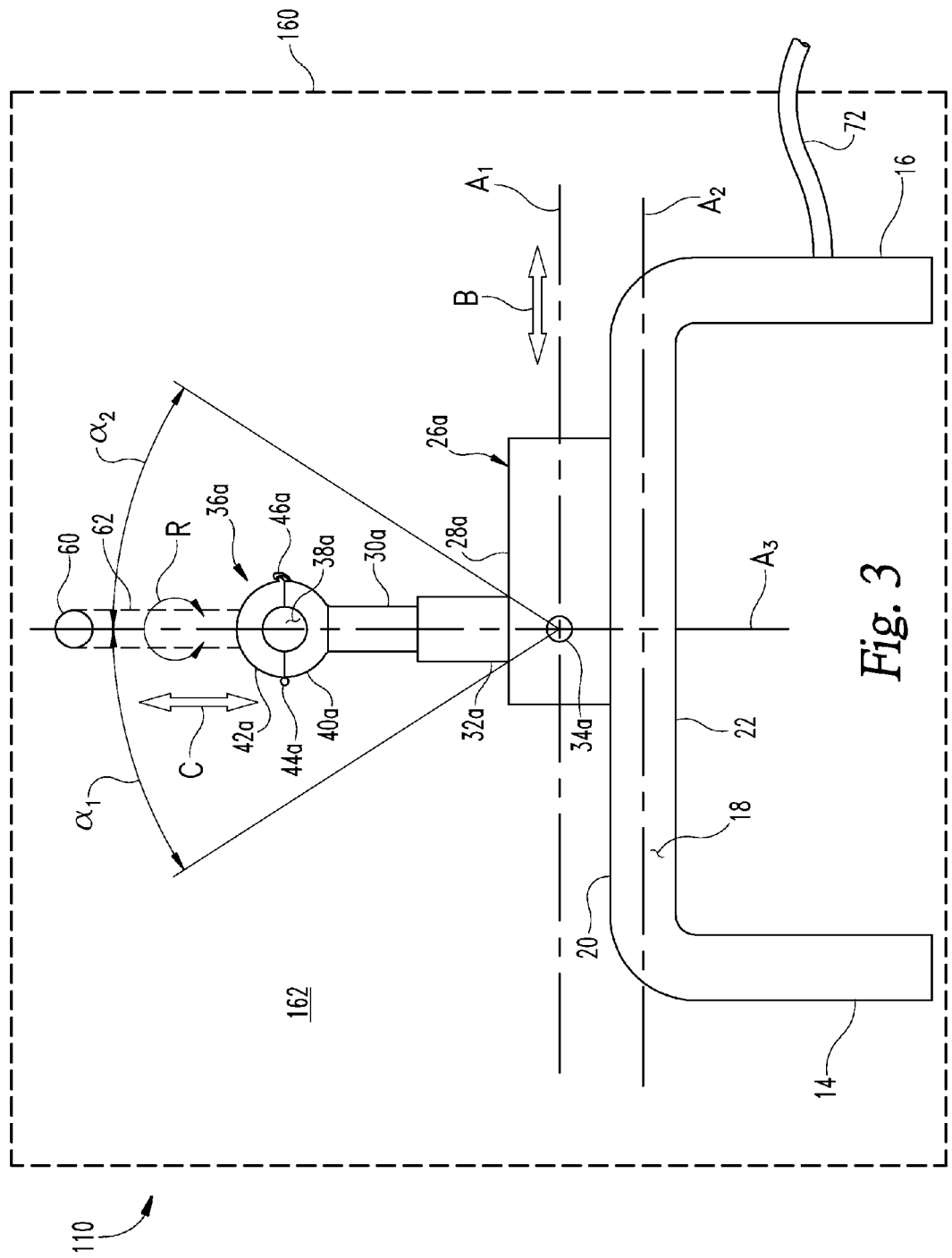
FIG. 3 is an end view of an alternative embodiment of a rod bending device.

Referring to FIG. 3, shown therein is an alternative embodiment of a device 110, where like numerals refer to like features of the device 10 previously described above. Unlike the device 10, which includes the heating element 60 positioned externally to the bending mechanism 11, the device 110 includes an environmental chamber or heating/cooling vestibule 160 defining an enclosed interior region 162 within which the bending mechanism 11 is positioned, and with the user interface 70 positioned external to the enclosed interior region 162. As should be appreciated, the environmental chamber 160 controls or regulates the temperature of the elongate rod member 90 as well as the bending mechanism 11. In one embodiment, the environmental chamber 160 controls or regulates temperature via convection heating using air, water or other heating media. It should be appreciated that the environmental chamber 160 may control or regulate temperature via various types of heating systems including, for example, coil resistance heating, metal oxide resistance heating, PTC (Positive Temperature Coefficient) heating, radiant heating, infrared heating, and/or conduction heating by way of direct contact with a heating element, just to name a few possibilities. Furthermore, in addition to controlling temperature via heating, the environmental chamber 160 may control or regulate temperature via cooling or refrigeration systems including, for example, convection cooling using air, water or other cooling media and/or conduction cooling by way of direct contact with a cooling element. Additionally, as should be appreciated, the environmental chamber 160 may be configured to control the temperature of the entire length of the elongate rod member 90 or the temperature of select axial portions of the elongate rod member 90.

The heat applied to the elongate rod member 90 by the heating element 60 or the environmental chamber 160 may aid in or facilitate bending of the elongate rod member 90 via relative movement of the engaging members 26a-26f to select positions that define a particular pathway or bend axis between the engaging members 26a-26f that corresponds to a particular rod curvature or contour. In one embodiment, the elongate rod member 90 is formed from one or more heat deformable materials. In a more specific embodiment, the heat deformable material(s) comprises one or more thermoplastic polymers. Examples of thermoplastic polymers include, for example, high molecular weight organic polymers. More particular examples of thermoplastic polymers include, without limitation, polycarbonate, polyketone, polyester, polyethylene, polyetheretherketone (PEEK), polyimide, polylactic acid, polypropylene, polystyrene, polysulfone, polyvinyl chloride, polyamide, poly(tetrafluoroethene), polyphthalamide, polybutylene and mixtures thereof, just to name a few possibilities. In one particular embodiment, the elongate rod member 90 is formed from a polyetheretherketone (PEEK) material. It is also contemplated that the elongate rod member 90 may be formed of other materials which, when heated, aid in or facilitate bending of the elongate rod member 90 to a desired configuration having a particular curvature or contour. For example, the elongate rod member 90 may be formed from one or metals or metal alloys including, for example, titanium, titanium alloys, chrome-cobalt (CrCo), stainless steel, or shape-memory materials such as Nitinol.

In other embodiments, the elongate rod member 90 may be formed as a composite material including, for example, a carbon or metal reinforced thermoplastic polymer or PEEK material, an inner core material surrounded by a thermoplastic polymer or PEEK outer sleeve material, or a thermoplastic polymer or PEEK inner core material surrounded by an outer sleeve material different from the inner core material. In one embodiment, the inner core material or the outer sleeve material may be formed of a metallic material such as, for example, titanium or stainless steel. However, the use of non-metallic inner core materials or non-metallic outer sleeve materials are also contemplated. In embodiments utilizing composite elongate rod members 90 that include a metallic inner core or a metallic outer sleeve, heating of the thermoplastic polymer or PEEK material may be accomplished by passing current through the metallic material. As should be appreciated, passing current through a resistive metallic material will cause the metallic material to heat up, which may in turn be used to heat the thermoplastic polymer or PEEK material to facilitate bending of the rod member. Additionally, in embodiments utilizing composite elongate rod members 90 that include a metallic inner core or a metallic outer sleeve, heating of the thermoplastic polymer or PEEK material may be accomplished by heating the metallic material via conduction heating (i.e., by placing a heat source in direct contact with the metallic material). As should be appreciated, the heated metallic material in turn applies heat to the thermoplastic polymer or PEEK material to facilitate bending of the rod member. Furthermore, in embodiments utilizing composite elongate rod members 90 that include an inner core, the inner core may be provided with an axial passage extending therethrough. In this embodiment, controlling the temperature of the thermoplastic polymer or PEEK material may be accomplished by passing a convective heating/cooling media through the axial passage to promote convective heat transfer between the media and the inner core member. As should be appreciated, the inner core member may in turn be used to control the temperature of the thermoplastic polymer or PEEK material to facilitate bending of the rod member.

As indicated above, the device 10 may be provided with a user interface 70. The user interface 70 may include a visual display 74 configured to provide information related to the bending mechanism 11, the heating element 60, the environmental chamber 160 and/or the elongate rod member 90 to a surgeon or other medical professionals. The user interface 70 may also be configured to provide other types of perceptible indications including audio or touch indications configured to provide information relative to the components of the device 10, 110 to a surgeon or other medical professionals. For example, the information provided by the user interface 70 may include an indication as to the temperature of the heat applied to the elongate rod member 90 by the heating element 60 or the environmental chamber 160, and/or the temperature of one or more portions of the elongate rod member 90. The user interface 70 may also provide a perceptible indication to the surgeon or other medical professionals once the elongate rod member 90 has reached an appropriate bending temperature, which in turn indicates when the bending mechanism 11 may be actuated to bend the elongate rod member 90. The visual display 74 may be of a Cathode Ray Tube (CRT) type, Liquid Crystal Display (LCD) type, plasma type, Organic Light Emitting Diode (OLED) type, a printer, or other types of visual displays that would occur to those skilled in the art. The user interface 70 may also include a user input 76 wherein, in one non-limiting example, a user may enter one or more commands to control the heat applied to the elongate rod member 90 by the heating element 60 or the environmental chamber 160 and/or the bending operation performed by the bending mechanism 11. The user input 76 may also include a keyboard, mouse or other pointing device, a voice recognition input subsystem, and/or different operator input apparatus that would occur to those skilled in the art. In one or more alternative embodiments, it is also contemplated that the device 10 may be provided without a user interface 70.

As indicated above, the engaging members 26a-26f are selectively positionable relative to one another and relative to the support platform 12 in a plurality of directions in order to define an arrangement defining a particular pathway or bend axis between the engaging portions of the engaging members 26a-26f that corresponds to a desired curvature or contour of the elongate rod member 90. Additionally, an initial straight configuration of the elongate rod member 90 may be positioned in the engaging portions of the engaging members 26a-26f when the engaging members 26a-26f are aligned with one another, as illustrated in FIG. 1. Once positioned in the engaging portions of the engaging members 26a-26f, a user may selectively position each of the engaging members 26a-26f relative to each other in order to bend the elongate rod member 90 in a desired manner. It should be appreciated that, given the ability for each of the engaging members 26a-26f to move in a plurality of directions relative to the support platform 12, as discussed above with respect to the engaging member 26a, the bending mechanism 11 is capable of forming bends or contours in the elongate rod member 90 in either two dimensions or three dimensions.

In one form of the present invention, once the elongate rod member 90 is suitably positioned in the engaging portions of the engaging members 26a-26f (FIG. 1), the heating element 60 is actuated and heat is applied to one or more portions of the elongate rod member 90. In one exemplary embodiment where the elongate rod member 90 is at least partially formed of a thermoplastic polymer such as PEEK, the heating element 60 heats the elongate rod member 90 until the thermoplastic polymer approaches or exceeds the glass transition temperature ($T_g$). As would be appreciated by those skilled in the art, as the thermoplastic polymer approaches or exceeds the glass transition temperature $T_g$, the material becomes less rigid and more flexible. As a corollary, once the elongate rod member 90 is heated in this manner, a user may initiate bending of the elongate rod member 90 via the bending mechanism 11. In one embodiment, a visual or audible indication may be provided to the user via the user interface 70 which indicates that the elongate rod member 90 has achieved a sufficient degree of flexibility, and that the user may begin bending/contouring of the elongate rod member 90 via actuation of the bending mechanism 11. After a sufficient amount of heat is applied to the elongate rod member 90 and the elongate rod member 90 has achieved a sufficient degree of flexibility, the user may initiate movement of the engaging members 26a-26f in one or more directions relative to one another and the support platform 12, as indicated by arrows B, C and R and angles $\alpha_1$ and $\alpha_2$ in FIG. 2. Relative movement of the engaging members 26a-26f may be gradually continued until the elongate rod member 90 is bent via actuation of the engaging members 26a-26f to provide the elongate rod member 90 with a select two-dimension or three-dimensional bend or contour.

As indicated above, the heating element 60 or the environmental chamber 160 heats the elongate rod member 90 to a temperature which tends to reduce rigidity and increase flexibility of the elongate rod member 90 to facilitate bending. It should be appreciated that the heating element 60 or the environmental chamber 160 may apply heat to the elongate rod member 90 prior to bending of the elongate rod member 90 and/or concurrently with bending of the elongate rod member 90. Once the elongate rod member 90 is bent to a desired configuration, the heating element 60 or the environmental chamber 160 is deactivated (or heating is reduced) to allow the elongate rod member 90 to cool to a temperature below the glass transition temperature $T_g$. As the elongate rod member 90 returns to a temperature below $T_g$, the rod material becomes more rigid and freezes the elongate rod member 90 in the desired shape/configuration to maintain the curvature or contour formed in the elongate rod member 90. A fan and/or a cooling element (discussed below) may also be used to decrease the temperature of the elongate rod member 90 in a controlled and expedited manner to facilitate prompt removal of the elongate rod member 90 from the bending mechanism 11. Once the elongate rod member 90 has cooled and has become sufficiently rigid, the elongate rod member 90 may be removed from the engaging portions of the engaging members 26a-26f. The elongate rod member 90 may then be engaged with the bone anchors attached to the spinal column and checked for proper fit. If the contour or curvature of the elongate rod member 90 must be adjusted to provide a more accurate fit, the elongate rod member 90 may be reinserted into the bending mechanism 11 of the device 10 to provide additional bending or contouring of the elongate rod member 90.

Figure 4:
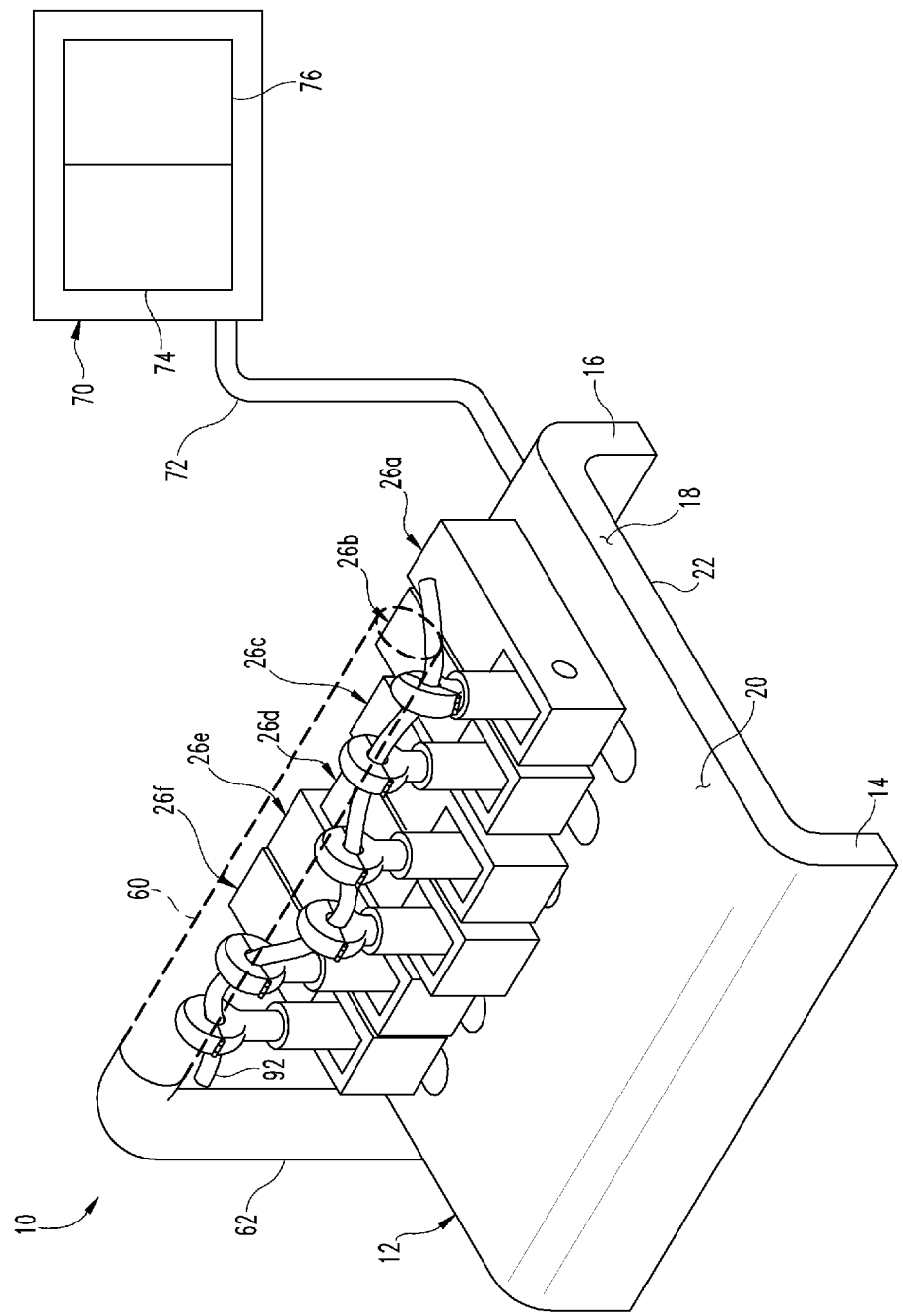
FIG. 4 is a perspective view of the rod bending device illustrated in FIG. 1, as engaged with a template member.

Referring now to FIG. 4, further details are illustrated regarding use of the device 10 according to another form for bending the elongate member 90. It should be appreciated that the device 110 may also be used in the following approach for bending the elongate member 90. As indicated above, in one form, the device 10 may be provided with one or more sensors that sense and record the relative positioning of each of the engaging members 26a-26f in a select arrangement. In this form, the engaging members 26a-26f may be moved relative to one another to provide an arrangement where a template member 92 may be positioned in the engaging portions of the engaging members 26a-26f. As illustrated in FIG. 4, the template member 92 has a select contoured profile. In one embodiment, the template member 92 generally has the same length, size and cross-sectional shape as the elongate rod member 90. The contoured profile of the template member 92 corresponds to the desired shape/contour of the elongate rod member 90 subsequent to bending by the device 10. In one embodiment, the template member 92 is formed of a material amenable to manual bending or bending via conventional bending tools or instruments. In a specific embodiment, the template member 92 is formed of a non-rigid, flexible material. In a more specific embodiment, the template member 92 is formed of aluminum or an aluminum alloy. The template member 92 may initially be provided in a straight configuration and then bent, either manually or with conventional bending tools or instruments, to a shape/contour that corresponds to the particular position of bone anchors attached to the spinal column to which the elongate rod member 90 will eventually be engaged. While the illustrated template member 92 has been bent to include multiple bends, some of which include a complex or compound orientation, it should be appreciated that in other embodiments, the template member 92 may include a single bend or one or more bends in addition to or in lieu of those specifically illustrated in FIG. 4.

As illustrated in FIG. 4, the engaging members 26a-26f are positioned relative to one another in an arrangement that corresponds to the contoured shape of the template member 92. At this point, the relative position/arrangement of the engaging members 26a-26f may be recorded via the sensors discussed above. In another form where the device 10 is provided without sensors configured to sense and record the relative positioning of the engaging members 26a-26f, it is contemplated that the relative positioning of the engaging members 26a-26f may be manually recorded. Once the relative positioning of the engaging members 26a-26f has been recorded, the template member 92 may be removed from the engaging portions of the engaging members 26a-26f, and the engaging members 26a-26f may be positioned in general alignment with each other (as illustrated in FIG. 1) where an elongate rod member 90 having a generally straight configuration may be positioned in the engaging portions of the engaging members 26a-26f. If desired, the heating element 60 may be actuated to heat the elongate rod member 90 in the manner described above, and each of the engaging members 26a-26f may be moved back to their marked and/or recorded position to bend the elongate rod member 90 to a shape/contour that corresponds to the shape/contour of the template member 92.

Figure 5:
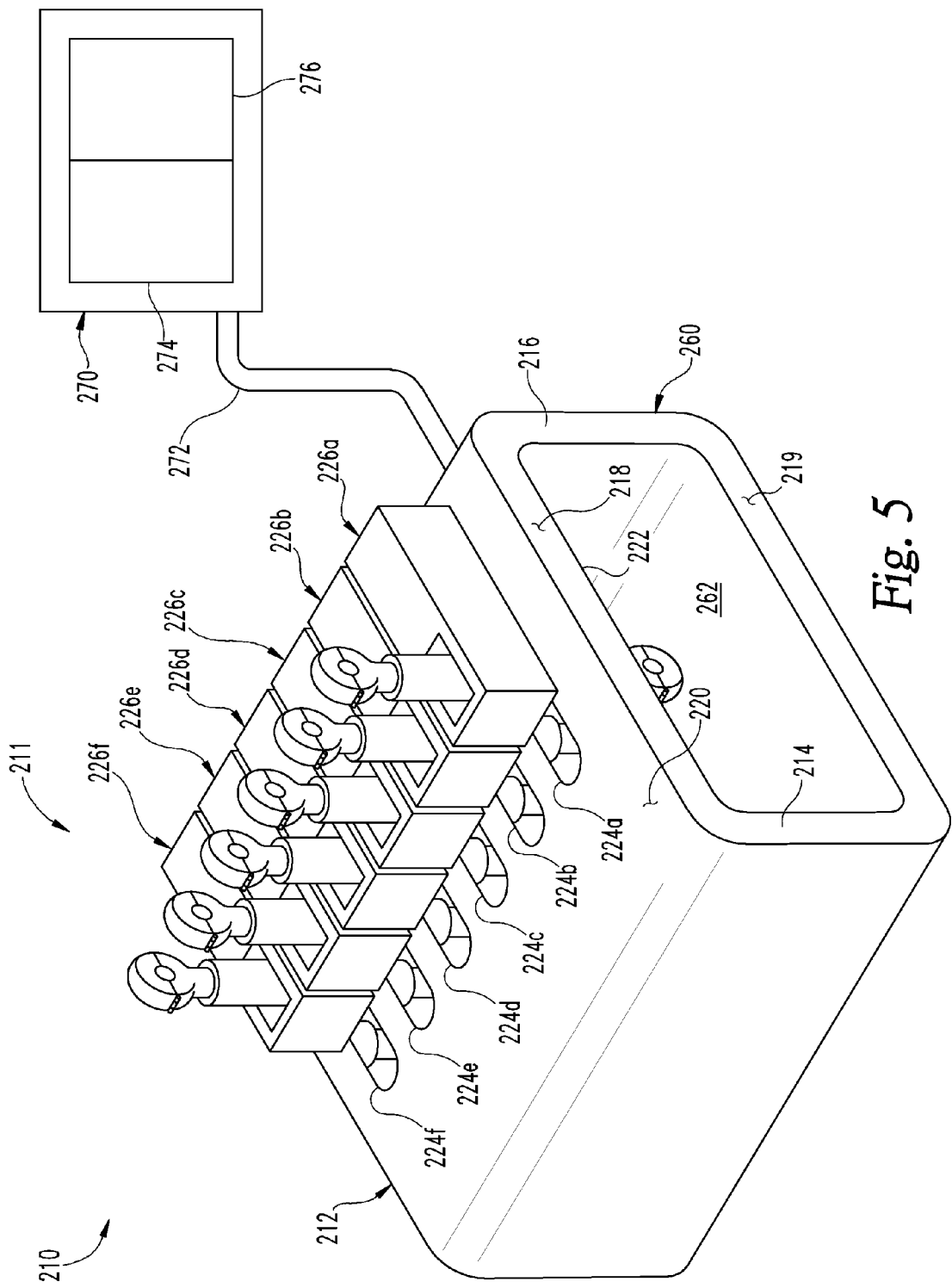
FIGS. 5 and 6 are perspective views of another embodiment of a rod bending device.
Figure 6:
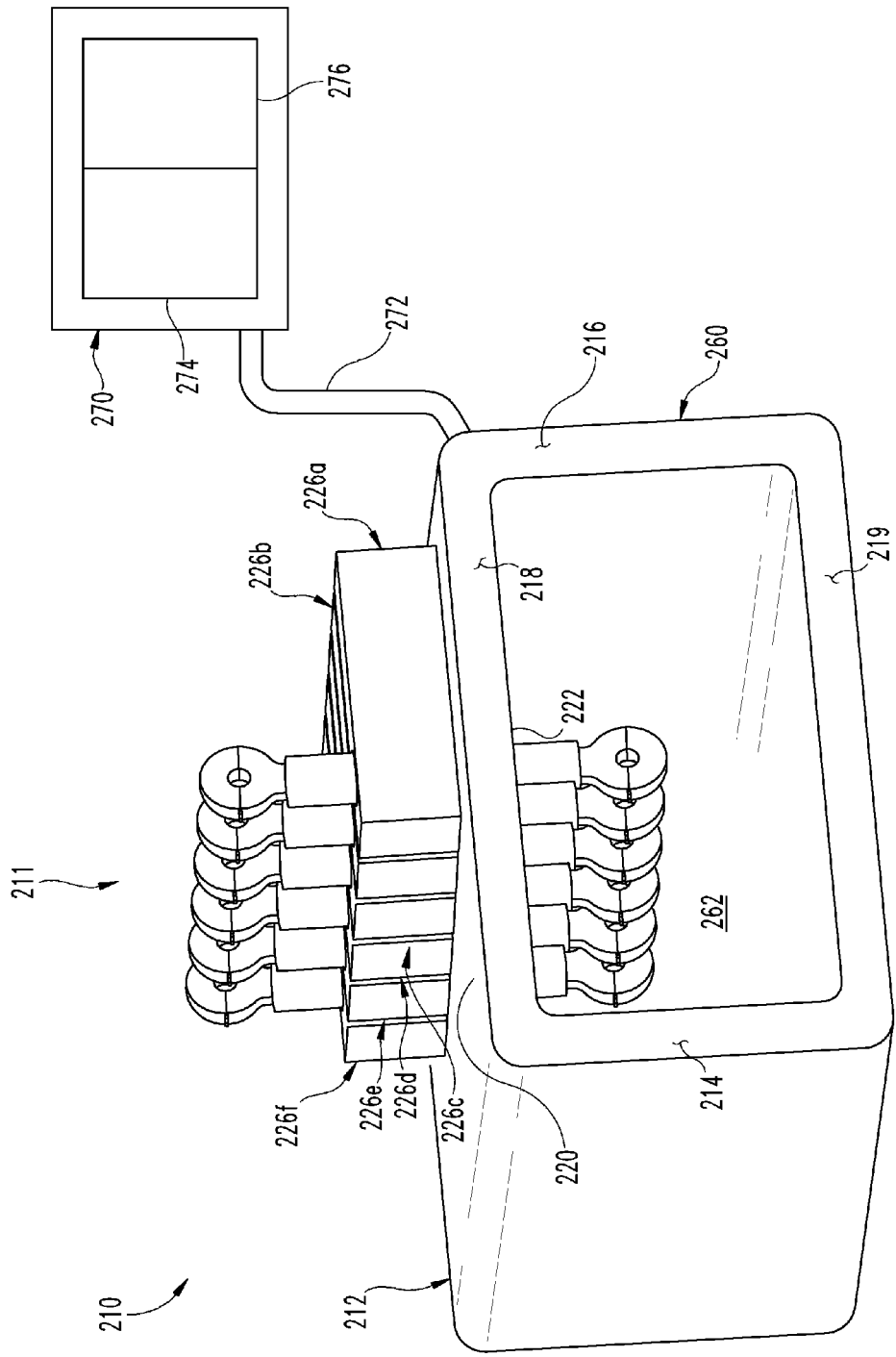

Referring now to FIGS. 5 and 6, illustrated therein is another embodiment of a device 210 for bending or contouring the elongate rod member 90. The device 210 includes a bending mechanism 211 operably coupled with a user interface 270 via a pathway 272. Further details regarding the user interface 270 will be set forth below. However, it should be appreciated that in other embodiments, the device 210 need not be provided with the user interface 270. The bending mechanism 211 is structured to bend or contour the elongate rod member 90 at one or more axial locations along the length of the elongate rod member 90. The bending mechanism 211 includes a support platform 212 including a first vertical leg 214 and a second vertical leg 216 that each extend from a first horizontal member 218. The first horizontal member 218 includes an upper surface 220 positioned opposite a lower surface 222. The support platform 212 also includes a second horizontal member 219 extending between the first leg 214 and the second leg 216. However, it should be appreciated that the illustrated configuration of the support platform 212 is exemplary, and that support platforms having other sizes, shapes and configurations are also contemplated. The first horizontal member 218 includes a plurality of elongated slots 224a-224f that extend through the horizontal member 218 between the upper and lower surfaces 220 and 222. The bending mechanism 211 further includes a plurality of engaging members 226a-226f associated with the elongated slots 224a-224f. Each of the engaging members 226a-226f is movable in a plurality of directions relative to the support platform 212, further details of which will be provided below in connection with the engaging member 226a. However, it should be appreciated that the details provided with respect to the engaging member 226a are also applicable to the other engaging members 226b-226f.

Figure 7:
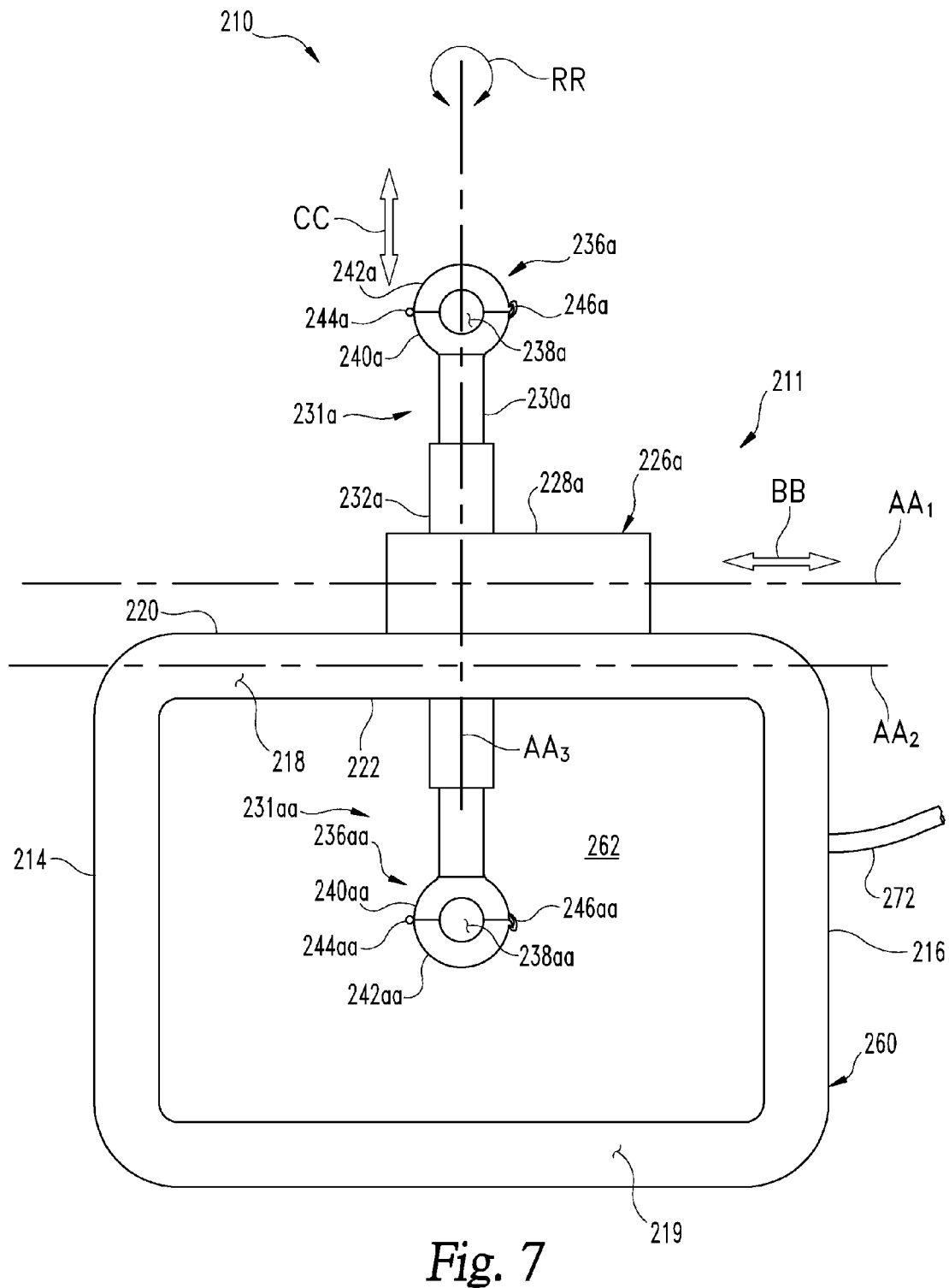
FIG. 7 is an end view of the rod bending device illustrated in FIGS. 5 and 6.

As shown in the end view of the device 210 in FIG. 7, the engaging member 226a includes a base member 228a that extends generally along an axis $AA_1$ that is substantially parallel to or inline with axis $AA_2$ along which the horizontal member 218 generally extends, although forms where the axis $AA_1$ and the axis $AA_2$ are oriented in different arrangements are also contemplated. The base member 228a is coupled to the horizontal member 218 and is arranged relative to the elongated slot 224a of the horizontal member 218 such that it is slidable to any number of positions along the length of the elongated slot 224a relative to the horizontal member 218, as indicated by directional arrow BB. It should be appreciated that various arrangements may be utilized to displace the engaging member 226a along the elongated slot 224a to select positions relative to the other engaging members 226b-226f and relative to the support platform 212. For example, in one embodiment, the engaging member 226a may be coupled to and movable by a rack and pinion mounting structure. The rack and pinion structure includes a rack portion coupled to the engaging member 226a, and a pinion portion coupled to the support platform 212. However, a reverse configuration is also contemplated wherein the rack portion is coupled to the support platform 212 and the pinion portion is coupled to the engaging member 226a. Each pinion portion includes a pinion gear that engages teeth formed along the rack portion. Rotation of the pinion gear displaces the engaging member 226a to position the engaging member 226a at a select location relative to the support platform 212. The pinion gear may be driven by various types of drives or actuators including, for example, an electric or pneumatic motor. In other embodiments, linear actuators or drives including, for example, pneumatic cylinders or electric screws, may be utilized to selectively position the engaging member 226a relative to the other engaging members 226b-226f and relative to the support platform 212. Still, further embodiments for facilitating selective positioning of the engaging member 226a include ball-detent mechanisms and releasably interlocking cams or tabs, just to name a few other possibilities.

The engaging member 226a also includes an elongate member 230a that includes an upper portion 231a positioned above the upper surface 220 of the horizontal member 218, and a lower portion 231aa positioned below the lower surface 222 of the horizontal member 218. The elongate member 230a is positioned in and coupled with a sleeve member 232a. In one non-illustrated form, the sleeve member 232a, and in turn the elongate member 230a, may be pivotably coupled to the base member 228a. The elongate member 230a extends along an axis $AA_3$ that extends transversely to the axes $AA_1$ and $AA_2$.

The elongate member 230a is axially translatable relative to the sleeve member 232a and the base member 228a along the axis $AA_3$, as indicated by directional arrow CC. Various arrangements for axially translating the elongate member 230a relative to the sleeve member 232a and the base member 228a are contemplated. For example, in one form, one or more linear actuators or drives may be utilized to axially translate and maintain positioning of the elongate member 230a relative to the sleeve member 232a and the base member 228a. In another form, it is contemplated that a rack and pinion arrangement may be disposed between the elongate member 230a and the sleeve member 232a in order to facilitate axial translation and positioning of the elongate member 230a at any of a number of positions along the axis $AA_3$. However, it should also be appreciated that in another form, the elongate member 230a may be manually axially-translated relative to the sleeve member 232a, and the base member 228a and the sleeve member 232a may be provided with a locking member, such as a set screw, that may be selectively engaged with the elongate member 230a in order to lock the axial positioning of the elongate member 230a relative to the sleeve member 232a and the base member 228a.

In addition to the foregoing, the elongate member 230a is also mounted relative to the base member 228a in a manner which allows the elongate member 230a to rotate about axis $AA_3$ relative to the sleeve member 232a and the base member 228a in the direction of arrows RR. Various arrangements for rotating the elongate member 230a relative to the sleeve member 232a and the base member 228a are contemplated. For example, in one form, one or more rotary actuators or drives may be utilized to rotate and maintain positioning of the elongate member 230a relative to the sleeve member 232a and the base member 228a. In another form, it is contemplated that the elongate member 230a may be manually rotated relative to the sleeve member 232a, and the base member 228a and the sleeve member 232a may be provided with a locking member, such as a set screw, that may be selectively engaged with the elongate member 230a in order to lock the relative positioning of the elongate member 230a and the sleeve member 232a.

The upper portion 231a of the elongate member 230a includes an engaging portion 236a that includes a circular-shaped opening 238a within which the template member 92 may be positioned, although it is also contemplated that the elongate rod member 90 may be positioned in the opening 238a. In the form illustrated in FIG. 7, the engaging portion 236a includes a pair of engaging elements 240a, 242a that are pivotally coupled to one another via a pivot or hinge element 244a. The engaging elements 240a, 242a may be maintained in a closed or captured position via a latch or lock element 246a. As should be appreciated, the template member 92 is engaged with the engaging portion 236a by pivoting the engaging element 242a to an open position, and laterally loading the template member 92 into half of the circular-shaped opening 238a defined by the engaging element 240a, followed by pivoting the engaging element 242a about the pivot element 244a to a closed position to capture the template member 90 within the circular-shaped opening 238a, thereby maintaining the engaging elements 240a, 242a in the closed or captured position via the latch element 246a.

The lower portion 231aa of the elongate member 230a includes an engaging portion 236aa that includes a circular-shaped opening 238aa within which the elongate rod member 90 may be positioned, although it is also contemplated that the template member 92 may be positioned in the opening 238aa. In the form illustrated in FIG. 7, the engaging portion 236aa includes a pair of engaging elements 240aa, 242aa that are pivotally coupled to one another via a pivot or hinge element 244aa. The engaging elements 240aa, 242aa may be maintained in a closed or captured position via a latch or lock element 246aa. As should be appreciated, the elongate rod member 90 is engaged with the engaging portion 236aa by pivoting the engaging element 242aa to an open position and laterally loading the elongate rod member 90 into half of the circular-shaped opening 238aa defined by the engaging element 240aa, followed by pivoting the engaging element 242aa about the pivot element 244aa to a closed position to capture the elongate rod member 90 within the circular-shaped opening 238aa, and maintaining the engaging elements 240aa, 242aa in the closed or captured position via the latch element 246aa.

As indicated above, in the form illustrated of FIG. 7, the openings 238a and 238aa include a circular shape. However, it should be appreciated that alternative configurations for one or both of the openings 238a and 238aa are also contemplated. For example, in other embodiments, one or both of the openings 238a and 238aa of the engaging portions 236a and 236aa may be provided with a polygonal, oval, or elliptical shape and configuration, or any other suitable shape or configuration that would occur to one of ordinary skill in the art. It should also be understood that one or both of the openings 238a and 238aa of the engaging portions 236a and 236aa, regardless of their shape and configuration, may be provided with a convexly-curved bottom surface having a saddle-like configuration to facilitate pivotal movement of the elongate rod member 90 or the template member 92 relative to the opening 238a or 238aa. Additionally, in one embodiment, one or both of the openings 238a and 238aa of the engaging portions 236a and 236aa are provided with a smooth surface finish to avoid scratching, gouging or otherwise damaging the outer surface of the elongate rod member 90 or the template member 92. However, in other embodiments, one or both of the openings 238a and 238aa of the engaging portions 236a and 236aa may be somewhat roughened and/or provided with one or more gripping elements to facilitate secure engagement with the elongate rod member 90 or the template member 92.

In view of the foregoing, it should be appreciated that each of the engaging members 226a-226f is movable in a plurality of directions relative to the support platform 212 and to one another in order to provide the elongate rod member 90 with a desired shape/contour, further details of which will be provided below. When the elongate rod member 90 is positioned in the upper or lower engaging portions of the engaging members 226a-226f, relative movement of the engaging members 226a-226f compressively engages the engaging members 226a-226f against the elongate rod member 90 to thereby bend the elongate rod member 90 to a desired contour or curvature along one or more portions of the rod length. As should be appreciated, the contour or curvature of the elongate rod member 90 is dictated or governed by the particular position and orientation of the individual engaging members 226a-226f relative to one another and relative to the elongate rod member 90. In addition to the foregoing, it should be appreciated that the upper and lower portions of the engaging members 226a-226f move simultaneously. In other words, the upper and lower portions of the engaging members 226a-226f move together such that the position of the lower portions of the engaging members 226a-226f relative to each other mirrors the relative positioning of the upper portions of the engaging members 226a-226 relative to each other. In an alternative form, it is contemplated that the lower portions of the engaging members 226a-226 may be independently moved relative to the upper portions of the engaging members 226a-226b. It should be appreciated that, given the ability for each of the engaging members 226a-226f to move in a plurality of directions relative to the support platform 212, the bending mechanism 211 is capable of forming bends or contours in the elongate rod member 90 in either two dimensions or three dimensions.

As collectively illustrated in FIGS. 5-7, the device 210 may be provided with an environmental chamber or heating/cooling vestibule 260 defining an enclosed interior region 262 within which the lower portions of the engaging members 226a-226f are positioned, and with the user interface 270 positioned external to the enclosed interior region 262. In one or more non-illustrated forms, it is contemplated that the device 210 may be provided with an alternatively configured heating element. As should be appreciated, the environmental chamber 260 controls or regulates the temperature of the elongate rod member 90 as well as a portion of the bending mechanism 211. In one embodiment, the environmental chamber 260 controls or regulates temperature via convection heating using air, water or other heating media. It should be appreciated that the environmental chamber 260 may control or regulate temperature via various types of heating systems including, for example, coil resistance heating, metal oxide resistance heating, PTC (Positive Temperature Coefficient) heating, radiant heating, infrared heating, and/or conduction heating by way of direct contact with a heating element, just to name a few possibilities. Furthermore, in addition to controlling temperature via heating, the environmental chamber 260 may control or regulate temperature via cooling or refrigeration systems including, for example, convection cooling using air, water or other cooling media and/or conduction cooling by way of direct contact with a cooling element. Additionally, as should be appreciated, the environmental chamber 260 may be configured to control the temperature of the entire length of the elongate rod member 90 or the temperature of select axial portions of the elongate rod member 90. The heat applied to the elongate rod member 90 by the environmental chamber 260 may aid in or facilitate bending of the elongate rod member 90 via relative movement of the engaging members 226a-226f to select positions that define a particular pathway or bend axis between the engaging members 226a-226f that corresponds to a particular rod curvature or contour.

As indicated above, the device 210 may be provided with a user interface 270. The user interface 270 may include a visual display 274 configured to provide information related to the bending mechanism 211, the environmental chamber 260 and/or the elongate rod member 90 to a surgeon or other medical professionals. The user interface 270 may also be configured to provide other types of perceptible indications including audio or touch indications configured to provide information relative to the components of the device 210 to a surgeon or other medical professionals. For example, the information provided by the user interface 270 may include an indication as to the temperature of the heat applied to the elongate rod member 90 by the environmental chamber 260, and/or the temperature of one or more portions of the elongate rod member 90. The user interface 270 may also provide a perceptible indication to the surgeon or other medical professionals once the elongate rod member 90 has reached an appropriate bending temperature, which in turn indicates when the bending mechanism 211 may be actuated to bend the elongate rod member 90. The visual display 274 may be of a Cathode Ray Tube (CRT) type, Liquid Crystal Display (LCD) type, plasma type, Organic Light Emitting Diode (OLED) type, a printer, or other types of visual displays that would occur to those skilled in the art. The user interface 270 may also include a user input 276 wherein, in one non-limiting example, a user may enter one or more commands to control the heat applied to the elongate rod member 90 by the environmental chamber 260 and/or the bending operation performed by the bending mechanism 211. The user input 276 may also include a keyboard, mouse or other pointing device, a voice recognition input subsystem, and/or different operator input apparatus that would occur to those skilled in the art. In one or more alternative embodiments, it is also contemplated that the device 210 may be provided without a user interface 270.

As indicated above, the engaging members 226a-226f are selectively positionable relative to one another and relative to the support platform 212 in a plurality of directions in order to define an arrangement defining a particular pathway or bend axis between the engaging portions of the engaging members 226a-226f that corresponds to a desired curvature or contour of the elongate rod member 90. In one approach for bending the elongate rod member 90 with the device 210, the elongate rod member 90 is provided in a straight configuration when initially positioned in the engaging portions of the lower portions of the engaging members 226a-226f. In one form, once the elongate rod member 90 has been positioned in the engaging portions of the lower portions of the engaging members 226a-226f, the environmental chamber 260 is actuated and heat is applied to one or more portions of the elongate rod member 90. In one exemplary embodiment where the elongate rod member 90 is at least partially formed of a thermoplastic polymer such as PEEK, the environmental chamber 260 heats the elongate rod member 90 until the thermoplastic polymer approaches or exceeds the glass transition temperature ($T_g$). As would be appreciated by those skilled in the art, as the thermoplastic polymer approaches or exceeds the glass transition temperature $T_g$, the material becomes less rigid and more flexible. As a corollary, once the elongate rod member 90 is heated in this manner, a user may initiate bending of the elongate rod member 90 via the bending mechanism 211. In one embodiment, a visual or audible indication may be provided to the user via the user interface 270 which indicates that the elongate rod member 90 has achieved a sufficient degree of flexibility, and that the user may begin bending/contouring of the elongate rod member 90 via actuation of the bending mechanism 211.

Figure 8:
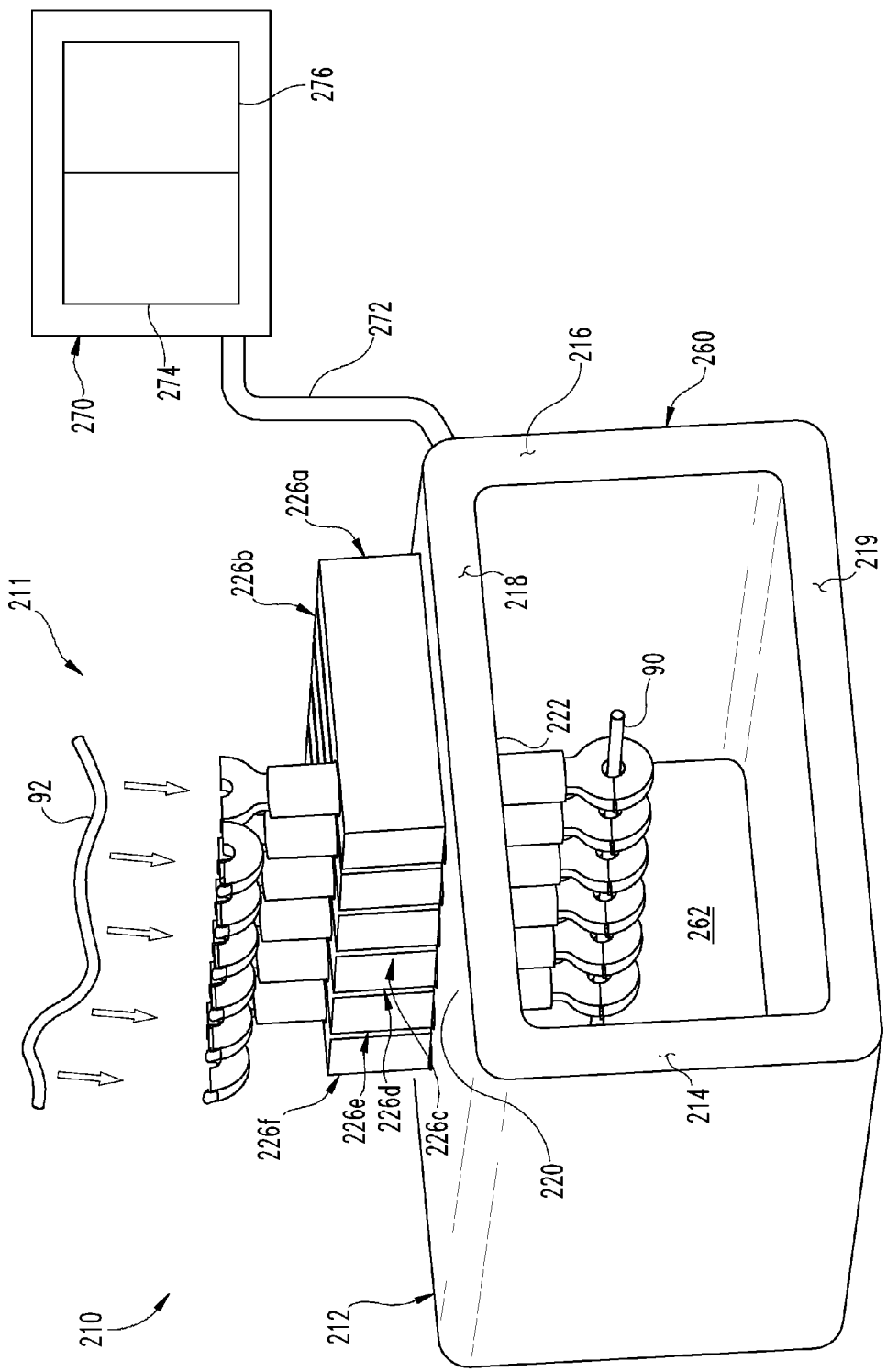
FIG. 8 is a perspective view of the rod bending device illustrated in FIGS. 5 and 6, as engaged with an elongate rod member.
Figure 9:
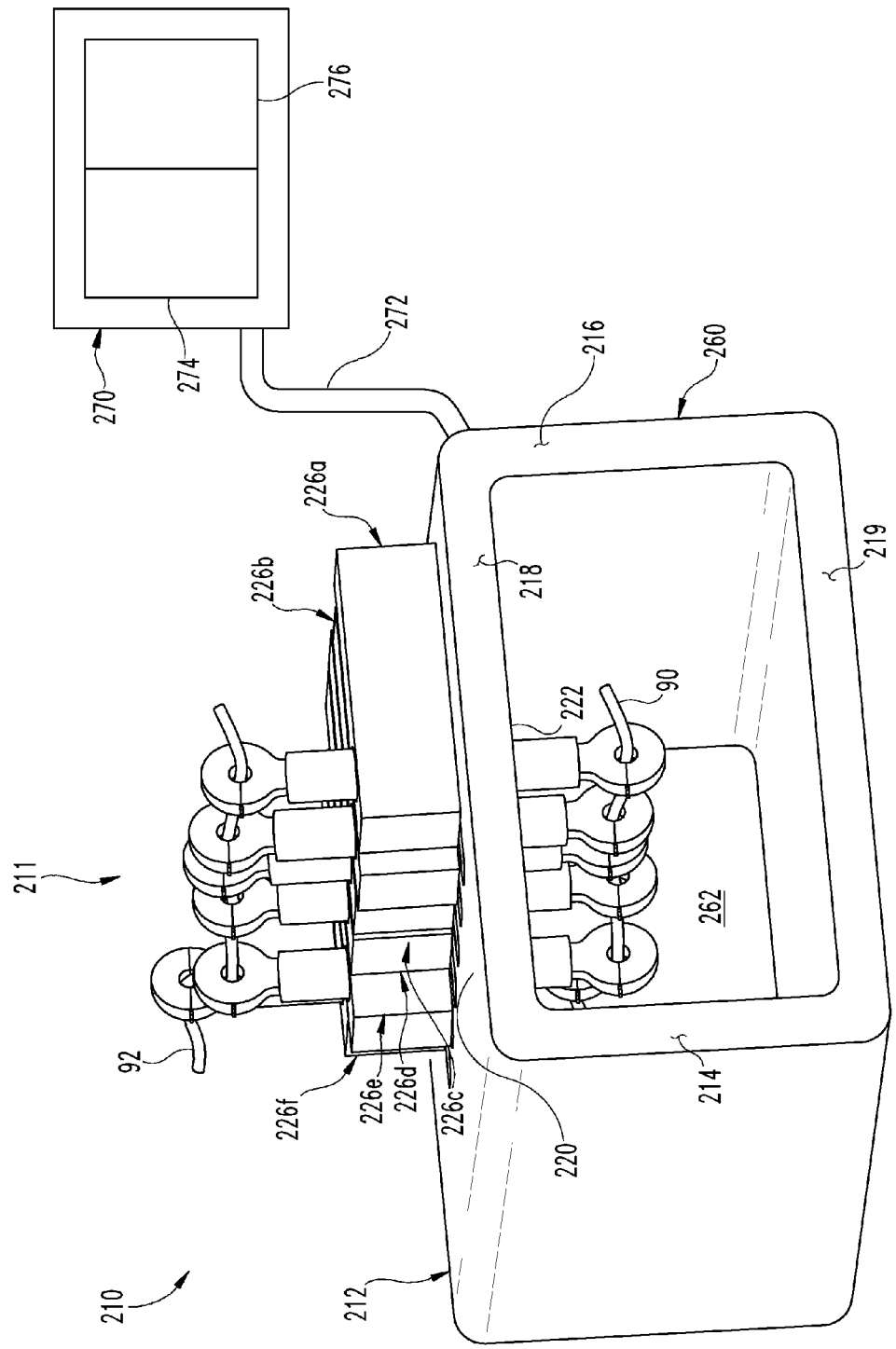
FIG. 9 is a perspective view of the rod bending device illustrated in FIGS. 5 and 6, as engaged with an elongate rod member and a template member.

After a sufficient amount of heat is applied to the elongate rod member 90 and the elongate rod member 90 has achieved a sufficient degree of flexibility, a user may begin arranging the engaging members 226a-226f relative to each other and the support platform such that the template member 92 may be positioned in the upper portions of the engaging members 226a-226f. The template member 92 includes a contoured profile that corresponds to the desired shape/contour of the elongate rod member 90 subsequent to bending by the device 210. As illustrated in FIG. 8, for example, the template member 92 has been bent to include multiple bends, some of which include a complex or compound orientation. However, it should be appreciated that in other embodiments, the template member 92 may include a single bend or one or more bends in addition to or in lieu of those specifically illustrated in FIG. 8. Since movement of the lower portions of the engaging members 226a-226f minors movement of the upper portions of the engaging members 226a-226f, it should be appreciated that the elongate rod member 90 positioned in the engaging portions of the lower portions of the engaging members 226a-226f will be bent to form a contoured profile that corresponds to the contoured profile of the template member 92 as the engaging portions of the upper portions of the engaging members 226a-226f are brought into engagement with the template member 92, as illustrated in FIG. 9.

As indicated above, the environmental chamber 260 heats the elongate rod member 90 to a temperature which tends to reduce rigidity and increase flexibility of the elongate rod member 90 to facilitate bending. It should be appreciated that the environmental chamber 260 may apply heat to the elongate rod member 90 prior to bending of the elongate rod member 90 and/or concurrently with bending of the elongate rod member 90. Once the elongate rod member 90 is bent and includes a configuration that corresponds to the configuration of the template member 92, the environmental chamber 260 is deactivated (or heating is reduced) to allow the elongate rod member 90 to cool to a temperature below the glass transition temperature $T_g$. As the elongate rod member 90 returns to a temperature below $T_g$, the rod material becomes more rigid and freezes the elongate rod member 90 in the desired shape/configuration to maintain the curvature or contour formed in the elongate rod member 90. A fan and/or a cooling element may also be used to decrease the temperature of the elongate rod member 90 in a controlled and expedited manner to facilitate prompt removal of the elongate rod member 90 from the bending mechanism 211. Once the elongate rod member 90 has cooled and has become sufficiently rigid, the elongate rod member 90 may be removed from the engaging portions of the lower portions of the engaging members 226a-226f. The elongate rod member 90 may then be engaged with the bone anchors attached to the spinal column and checked for proper fit. If the contour or curvature of the elongate rod member 90 must be adjusted to provide a more accurate fit, the elongate rod member 90 may be reinserted into the bending mechanism 211 of the device 210 to provide additional bending or contouring of the elongate rod member 90.

In an alternative form of the device 210, it is contemplated that the lower portions of the engaging members 226a-226f may be independently moved relative to the upper portions of the engaging members 226a-226f in each of the directions AA, BB and RR illustrated in FIG. 7. However, it is also contemplated that the upper and lower portions of the engaging members 226a-226f may be pivoted relative to their respective base member, as discussed above with regard to the arrangement of the sleeve member 32a relative to the base member 28a of the device 10. In the form where the upper and lower portions of the engaging members 226a-226f may be moved independently from the other, the upper portions of the engaging members 226a-226f may be arranged relative to one another such that the template member 92 may be positioned in the engaging portions of the upper portions of the engaging members 226a-226f. The device 210 may be further arranged to sense the relative positioning of the upper portions of the engaging members 226a-226f relative to one another and the support platform 212, and to move the lower portions of the engaging members 226a-226f relative to one another and the support platform 212 to an arrangement that corresponds to the arrangement and orientation of the upper portions of the engaging members 226a-226f. Similarly, when the elongate rod member 90 is positioned in the engaging portions of the lower portions of the engaging members 226a-226f and the lower portions of the engaging members 226a-226f are moved in this manner, the elongate rod member 90 is bent to provide a curved contoured profile that corresponds to the curved or contoured profile of the template member 92. If desired, the environmental chamber 260 may be actuated to heat the elongate rod member 90 before the lower portions of the engaging members 226a-226f are moved to bend the elongate rod member 90. Once the elongate rod member 90 has been bent to a desired configuration, the environmental chamber 260 may also be used to selectively control cooling of the elongate rod member 90.

It should also be appreciated that forms in which the device 210 is used to bend the elongate rod member 90 without utilizing the template member 92 are also contemplated. For example, in one form, it is contemplated that the elongate rod member 90 may be positioned in the engaging portions of the upper or lower portions of the engaging members 226a-226f followed by selectively positioning the upper or lower portions of the engaging members 226a-226f relative to each other in order to bend the elongate rod member 90 in a desired manner.

Figure 10:
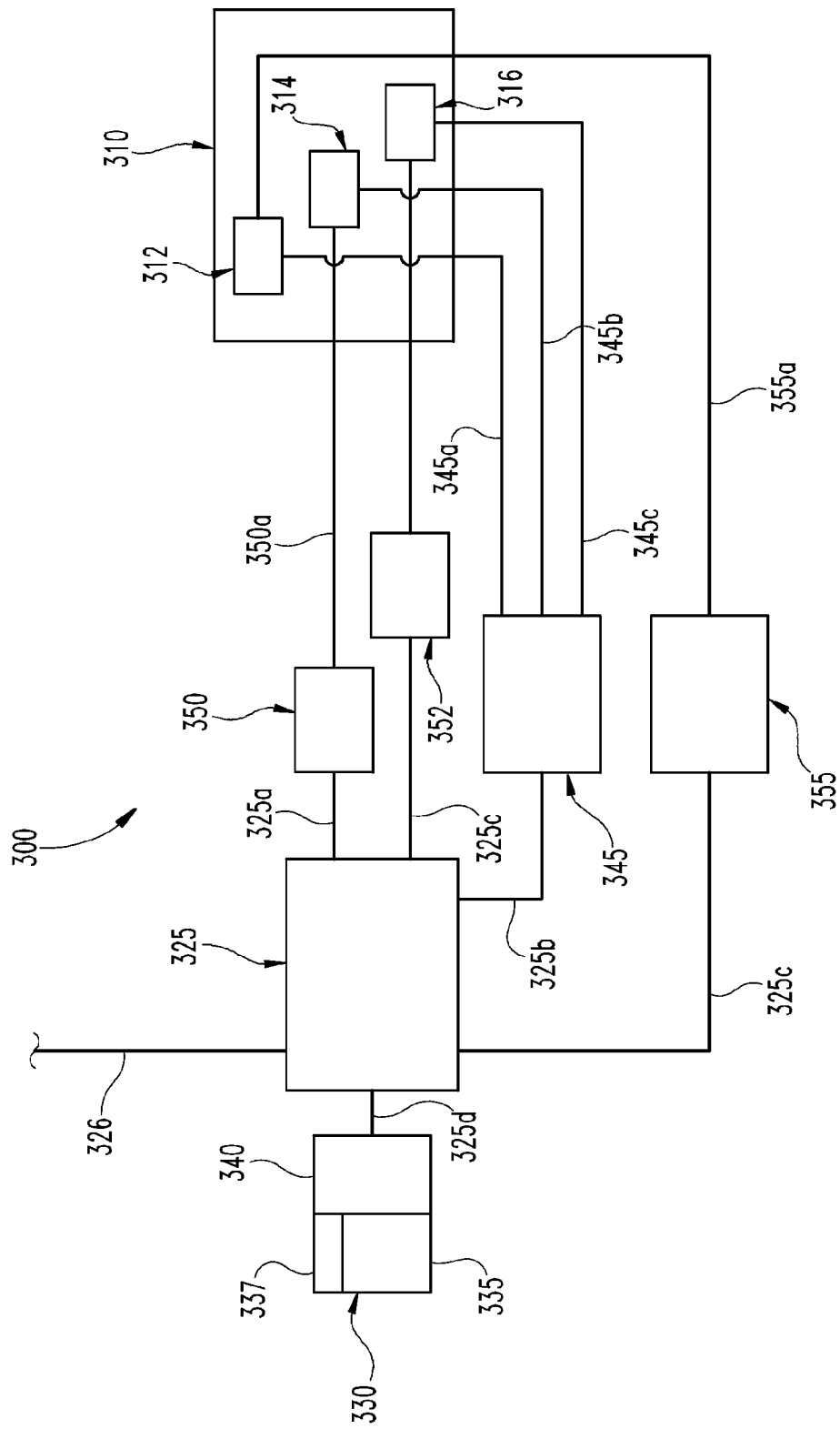
FIG. 10 is a schematic diagram illustrating a system according to one form of the invention for bending/contouring an elongate rod member.

Referring now to FIG. 10, shown therein is a schematic illustration of a system 300 for bending the elongate rod member 90 to a desired curvature or contour. The system 300 includes a rod bending device 310 that generally includes a bending mechanism 312 and a heating element 314. Additionally, in other embodiments, the system 300 may be configured to control aspects of bending the elongate rod member 90 without heating the elongate rod member 90 (i.e., forms in which the heating element 314 is omitted). The rod bending device 310 may optionally be provided with a cooling element 316. It should be appreciated that the bending mechanism 312 may be configured similar to the bending mechanism 11 illustrated and described above with regard to the device 10, 110, or the bending mechanism 211 illustrated and described above with regard to the device 210. Additionally, it should be understood that various features and characteristics described above with respect to the heating element 60 and the environmental chambers 160, 260 are equally applicable to the heating element 314 and/or the cooling element 316. It should also be understood that one or more features associated with the heating element 314 and the cooling element 316 may be incorporated into an integrated heating/cooling element.

Besides the rod bending device 310, the system 300 may also be provided with a controller 325, a user interface 330, a sensing arrangement 345, a heat source 350, and an optional cooling source 352. The system 300 may also include one or more actuating members 355 for regulating or controlling actuation of the bending mechanism 312.

The sensing arrangement 345 includes one or more sensors structured to monitor one or more operating functions associated with the device 310. For example, the operating functions monitored by the sensing arrangement 345 may include sensing/monitoring of the heating function provided by the heating element 314 and/or sensing/monitoring of the cooling function provided by the cooling element 316 via one or more temperature sensors or thermocouples. Additionally, the operating functions monitored by the sensing arrangement 345 may also include sensing/monitoring of the pressure applied to the elongate rod member 90 by the bending mechanism 312 and/or the actuating members 355 via one or more feedback or pressure sensors, and/or sensing/monitoring of the relative position/orientation of the rod engaging members associated with the first and second engaging portions via one or more position sensors.

In the illustrated embodiment, the sensing arrangement 345 is electronically coupled to the bending mechanism 312 via pathway 345a and includes one or more feedback or pressure sensors configured for sensing/monitoring the amount of pressure applied to the elongate rod member 90 by the bending mechanism 312. The sensing arrangement 345 is electronically coupled with the heating element 314 via pathway 345b, and includes one or more temperature sensors or thermocouples configured for sensing/monitoring the heating function provided by the heating element 314, and/or to directly sense/monitor the temperature of one or more portions of the elongate rod member 90. The sensing arrangement 345 is electronically coupled with the cooling element 316 via pathway 345c, and includes one or more temperature sensors or thermocouples configured for sensing/monitoring the cooling function provided by the cooling element 316, and/or to directly sense/monitor the temperature of one or more portions of the elongate rod member 90. The sensing arrangement 345 may also be electronically coupled to the bending mechanism 312 via a pathway connected to one or more position sensors configured for sensing/monitoring the relative position of the engaging members. In one embodiment, the sensing arrangement 345 may be structured to sense/monitor the temperature of the heating element 314 and the cooling element 316. In another embodiment, the sensing arrangement 345 may be structured to directly sense/monitor the temperature of one or more portions of the elongate rod member 90. In a further embodiment, the sensing arrangement 345 may be structured to sense/monitor the temperature of the bending mechanism 312. The sensing arrangement 345 is further structured to provide an electronic sensor signal corresponding to the sensed pressure, temperature and/or position to the controller 325 along pathway 325b to the controller 325.

In one embodiment, the controller 325 operates in accordance with operating logic to receive and process the sensor signals to determine if a change in temperature, pressure and/or position is required. It may be desirable to maintain a particular balance of the temperature and pressure to avoid undesired deformation or fracturing/breaking of the elongate rod member 90. For example, depending on its form and material composition, excessive heat may possibly cause the elongate rod member 90 to melt and/or degrade or negatively affect the material properties of the elongate rod member 90, while excessive pressure may cause the elongate rod member 90 to improperly deform, break and/or degrade or negatively affect the material properties of the elongate rod member 90. In one embodiment, the controller 325 is comprised of one or more components that may be configured as a single unit, or may alternatively be distributed among two or more units. Such components may be of a solid state, electromagnetic, optical, and/or other configurations that would occur to those skilled in the art. The controller 325 may include analog circuitry, digital circuitry, and/or a hybrid combination of both. In one embodiment, the controller 325 is of the programmable variety that executes algorithms and processes data in accordance with operating logic defined by programming instructions (i.e., software or firmware). Alternatively or additionally, the operating logic for the controller 325 may be at least partially defined by hardwired logic or other hardware.

As further illustrated in FIG. 10, the controller 325 includes a power supply 326 which may supply power to the controller 325 from an external source, such as an electrical socket. In another non-illustrated embodiment, a power supply may be located internally within the controller 325 and may be provided, for example, in the form of one or more electrochemical cells or a battery of cells. It should be appreciated that the controller 325 may be modified for use with a DC power source or an AC power source, and that the modification of components may be dependent upon the availability of one or more forms of the power source. Additional variations to the controller 325 will become apparent with respect to various configurations of the system 300. It should also be appreciated that the controller 325 may provide power to the other components of the system 300 such as the user interface 330, the heat source 350, the cooling source 352, the bending mechanism 312, the actuating member(s) 355 and/or the sensing arrangement 345. Alternatively, power may be provided to one or more of these components directly via a dedicated power source.

After the controller 325 receives and processes one or more of the sensor signals, one or more controller output signals are sent to the user interface 330 via pathway 325d. In one example, the controller output signals may include a temperature output signal, a pressure output signal and/or a position output signal corresponding to the relative positioning of the engaging members. The user interface 330 may include a visual display 335 and/or an audio component 337 configured to provide one or more indications corresponding to the output signal to a user, and which may identify any necessary changes, if any, to the temperature, pressure and/or position. The visual display 335 may be of a Cathode Ray Tube (CRT) type, Liquid Crystal Display (LCD) type, plasma type, Organic Light Emitting Diode (OLED) type, a printer, or other types of output devices as would occur to those skilled in the art. The user interface 330 may also include a user input 340 wherein a user may enter commands, data, or programming instructions. Additionally or alternatively, a user may enter other information at the user input 340 relevant to the bending process, such as the type of material from which the elongate rod member 90 is formed and/or a desired amount of heat to be applied by the heating element 314, just to name a few possibilities. The user input 340 may include a keyboard, mouse or other pointing device, a voice recognition input subsystem, and/or different operator input apparatus as would occur to those skilled in the art.

As one example of a response to the indication provided by the visual display 335 and/or the audio component 337, the user may provide an input signal at the user input 340 which indicates that the temperature of the heat provided by the heating element 314 needs to be increased, decreased or maintained. The input signal may be transmitted to the controller 325 along the pathway 325d, received and processed by the controller 325, and a corresponding output signal may be provided by the controller 325 to the heat source 350 and/or the cooling source 352 via pathways 325a, 325c. The heat source 350 and/or the cooling source 352 then control the heating element 314 and/or the cooling element 316, which in turn controls/regulates the temperature of the elongate rod member 90. While the heat source 350 and the heating element 314 have been illustrated as separate components, it should be appreciated that in alternative embodiments, the heat source 350 and the heating element 314 may be provided as a single, integrated component. Additionally, while the cooling source 352 and the cooling element 316 have been illustrated as separate components, it should be appreciated that in alternative embodiments, the cooling source 352 and the cooling element 316 may be provided as a single, integrated component. Furthermore, it should be appreciated that in alternative embodiments, the heating element 314 and the cooling element 316 may also be provided as a single, integrated component. Moreover, as alternatives to the foregoing, the controller 325 may automatically control/regulate the heating element 314 and the cooling element 316 in response to the sensor signal without any user input, or a user may directly input a temperature change at the heat source 350 or the cooling source 352 in response to the indication provided by the visual display 335 and/or the audio component 337.

As an additional or alternative response to the output signal provided by the display 335, the user may increase, decrease or maintain the amount of pressure applied to the elongate rod member 90 by the bending mechanism 312. Alternatively, the system 300 may include an actuating member 355 structured to provide and control/regulate actuation of the bending mechanism 312 and/or the relative positions of the engaging members. In one form, the actuating member(s) 355 may include an electronic or pneumatic motor configured to control positioning of the engaging members relative to one another and relative to the support platform. In another form, the actuating member(s) 355 may be provided as a hydraulic arrangement including a hydraulic device configured to provide and regulate actuation of the bending mechanism 312. In one particular aspect of this form, the device may be configured to provide back pressure or an electronic feedback signal in response to an amount of force applied by a user to the bending mechanism 312 to limit the amount of force applied by, and/or the rate of actuation of, the bending mechanism 312. In still other embodiments, the actuating member(s) 355 may be provided with other types of mechanical arrangements configured to provide and regulate actuation of the bending mechanism 312.

When the system 300 includes actuating member(s) 355, the user may provide an input signal at the user input 340 which indicates the desired amount of pressure to be applied to the elongate rod member 90 by the bending mechanism 312. Alternatively, the user may provide an input signal at the user input 340 which indicates the desired relative positioning of the engaging members. The input signal may be transmitted to the controller 325 along the pathway 325*d*, received and processed by the controller 325, and a corresponding output signal may be provided by the controller 325 to the actuating member(s) 355 via pathway 325*c*. The actuating member(s) 355 then communicate(s) with the bending mechanism 312 via pathway 355*a* in correspondence to the output signal to regulate the amount of pressure applied on the elongate rod member 90 by the bending mechanism 312 or otherwise control the relative positioning of the engaging members of the bending mechanism 312. While the actuating member(s) 355 and the bending mechanism 312 have been illustrated as separate components, it should be appreciated that in alternative embodiments, these separate components may be combined into a single, integrated component. Furthermore, as alternatives to the foregoing, the controller 325 may automatically regulate the pressure applied to the elongate rod member 90 by the bending mechanism 312 in response to a sensor signal without any user input, or a user may directly input a pressure change at the actuating member(s) 355 in response to the indication provided by the display 335 and/or the audio component 337.

As indicated above, the controller 325 may be programmed to operate in accordance with operating logic to automatically or semi-automatically control various functional and operational aspects of the system 300. In other words, the controller 325, in cooperation with the user interface 330 and the sensing arrangement 345, may be programmed to automatically monitor and control various functional and operational aspects of the rod bending device 310 including the bending mechanism 312, the heating element 314 and/or the cooling element 316. In one embodiment, the controller 325 is programmable to contour or bend the elongate rod member 90 to define two-dimension or three-dimensional curvatures, including a single curved portion or multiple curved portions. Additionally, the controller 325 may be programmed to provide the elongate rod member 90 with one or more linear portions so as to provide the elongate rod member 90 with a curvilinear configuration. In another embodiment, the controller 325 is programmable to contour or bend the elongate rod member 90 using a predefined heating, bending and/or cooling profile that automatically controls heating of the elongate rod member 90 via the heating element 314, bending of the elongate rod member 90 via the bending mechanism 312, and/or cooling of the elongate rod member 90 via the cooling element 316. In a further embodiment, the controller 325 is programmable to bend the elongate rod member 90 that is formed of a particular material or combination of materials (i.e., PEEK, a PEEK composite material, titanium, a titanium alloy, CoCr, Nitinol, etc.), that is provided with a particular outer cross-sectional shape (i.e., circular, elliptical, square, rectangular, polygonal, etc.), and/or that is provided with a particular outer cross-sectional size, and/or a particular rod configuration (i.e., solid, hollow, inner core within an outer sleeve, etc.). In each of these embodiments, the controller 325 may be programmed via the user interface 330 and/or may be programmed via loading a program or operating logic from internal memory of the controller 325, from a memory media or from a remote memory location.

Furthermore, the controller 325, in cooperation with the sensing arrangement 345, may be programmed to limit or regulate various functional and operational aspects of the rod bending device 310 to prevent damage or weakening of the elongate rod member 90 and/or one or more elements or components of the system 300. For example, the controller 325 may be programmed to limit or regulate the bending pressure exerted onto the elongate rod member 90 via the rod bending device 310, to limit or regulate the amount of heat applied to the elongate rod member 90 via the heating element 314, and/or to limit or regulate the rate of heating or cooling of the elongate rod member 90 via the heating element 314 and/or the cooling element 316. As should be appreciated, programming the controller 325 to limit or regulate various functional and operational aspects of the rod bending device 310 may prevent breakage or compromising the mechanical strength of the elongate rod member 90 and/or one or more elements or components of the system 300.

In a further embodiment, the system 300 is configured to provide real-time, dynamic control of the rod bending process. It may be particularly desirable to maintain a balance of the temperature and pressure to avoid undesired deformation or fracturing/breaking of the elongate rod member 90. For example, the system 300 may be configured to automatically control the amount of heat and/or pressure applied to the elongate rod member 90 during the bending process to avoid undesired deformation of the elongate rod member 90 or a negative effect on the material properties of the elongate rod member 90. As should be appreciated, excessive heat or an excessive heating rate may possibly cause the elongate rod member 90 to melt and/or degrade or negatively affect the material properties of the elongate rod member 90, while excessive pressure may cause the elongate rod member 90 to improperly deform, break and/or degrade or negatively affect the material properties associated with the elongate rod member 90. In one particular form of control, the system 300 is configured to gradually increase the bend/curve in the elongate rod member 90 until a desired curvature or contouring of the elongate rod member 90 is achieved. Once the desired configuration is achieved, the system 300 is operable to selectively eliminate or reduce the heat and/or pressure applied to the elongate rod member 90. Particularly, the system 300 may eliminate or reduce the application of heat to the elongate rod member 90 via regulation of the heating elements 314 and/or the cooling element 316 to in turn adjust the temperature of the elongate rod member 90 to a target temperature, and deactuation of the bending mechanism 312 and removal or reduction of the pressure applied to the elongate rod member 90. The elongate rod member 90 may then be removed from the bending mechanism 312 and checked for proper fit in an orthopedic construct. Alternatively, the elongate rod member 90 may be repositioned in the bending mechanism 312, and one or more additional bends may be formed in the elongate rod member 90.

Still other modifications and variations to the system are contemplated. As indicated above, the system 300 may be provided with a sensing arrangement 345 including sensors structured to monitor one or more functional or operational aspects associated with the device 310, including the sensing/monitoring of the heating function provided by the heating element 314 and/or sensing/monitoring of the cooling function provided by the cooling element 316 via one or more temperature sensors or thermocouples. After the elongate rod member 90 has been loaded into/onto the device 310, the elongate rod member 90 is heated to a predetermined temperature, and is preferably heated at a predetermined heating rate. Once the elongate rod member 90 has been heated to a predetermined temperature or temperature range, the user interface 330 may generate a perceptible signal (i.e., a visual signal or an audible signal) that indicates that the elongate rod member 90 is ready for bending. The bending mechanism 312 may then by actuated, either automatically or manually, to bend the elongate rod member 90 to a particular contour. The temperature of the elongate rod member 90 may be monitored during the bending process and the temperature of the elongate rod member 90 adjusted via actuation of the heating element 314 and/or the cooling element 316 to maintain the elongate rod member 90 within an acceptable temperature range. After the elongate rod member 90 is bent, the temperature of the elongate rod member 90 may be reduced via actuation of the cooling element 316, and is preferably cooled at a predetermined cooling rate. Controlled cooling of the elongate rod member 90 provides increased stability and allows for prompt removal of the elongate rod member 90 from the bending device 310.

In another embodiment, a device for bending an elongate member is provided and includes a bending mechanism having a plurality of engaging members. Each of the plurality of engaging members is selectively positionable relative to a portion of the bending mechanism structured for receiving the elongate member. The device also includes a heating element arranged to apply heat to the elongate member when the elongate member is positioned in the bending mechanism.

In still another embodiment, a device for bending an elongate member is provided, including a bending mechanism having at least two sets of engaging members which are arranged orthogonally to each other. Each of the engaging members is selectively positionable relative to a portion of the bending mechanism structured for receiving the elongate member. In one aspect, the device also includes a heating element arranged to apply heat to the elongate member when the elongate member is positioned in the bending mechanism.

In another form, it is contemplated that the bending devices 10, 110 and 210 may be configured to bend the elongate rod member 90 to correspond to a computer generated model having a contoured configuration that corresponds to the configuration of the elongate rod member 90 necessary to be engaged with one or more bone anchors engaged to bones or bony structures, such as one or more vertebrae of the spinal column. In one aspect of this form, the computer generated model is extrapolated from x-ray or other images taken of the anatomical location where the elongate rod member 90 will eventually be implanted. Other forms and applications for generating the computer model are also contemplated.

Alternative configurations and uses of the systems and devices described herein are also contemplated. For example, in one or more forms the systems and devices described herein may also be used in surgical procedures involving animals, or in demonstrations for training, education, marketing, sales and/or advertising purposes. Additionally, the systems, devices and methods described herein may also be used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present invention, and is not intended to make the present invention in any way dependent upon such theory, mechanism of operation, proof or finding. It should be understood that while the use of the word preferable, preferably or preferred in the description above indicates that the feature so described may be more desirable, it nonetheless may not be necessary, and embodiments lacking the same may be contemplated as within the scope of the application, that scope being defined by the claims that follow. In reading the claims, it is intended that when words such as "a", "an", "at least one", and "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A device for bending a rod member used in a medical procedure, comprising:
   a support platform; and
   a plurality of engaging members positioned on said support platform, each of said plurality of engaging members includes a base member and an elongate member coupled with said base member, the elongate members each having an engaging portion configured for positioning in contact with said rod member, the elongate members being movable in at least three directions relative to said support platform to form one or more bends in said rod member and said base member being independently movable relative to said elongate member and said support platform.

2. The device of claim 1, wherein each of said base members is slidable along a first axis extending substantially parallel to a first surface of said support platform.

3. The device of claim 2, wherein each of said elongate members extends along a second axis, said second axis extending transverse to said first axis.

4. The device of claim 3, wherein each of said elongate members is axially slidable along said second axis relative to said support platform and said base members.

5. The device of claim 4, wherein each of said elongate members is axially rotatable about said second axis relative to said support platform and said base members.

6. The device of claim 5, wherein each of said elongate members is pivotably coupled to a respective one of said base members.

7. The device of claim 1, wherein said engaging portion of each of said engaging members is axially spaced from a first surface of said support platform.

8. The device of claim 7, wherein each of said engaging portions includes an opening sized and configured to receive a portion of said rod member therein.

9. The device of claim 8, wherein each of said engaging members further includes a closure member positionable between an open configuration for positioning said portion of said rod member in said opening and a closed configuration for fully enclosing said portion of said rod member in said opening.

10. The device of claim 1, further comprising a heating member structured and arranged to apply heat to select portions of said rod member to facilitate bending of said select portions by said plurality of engaging members to form said one or more bends.

11. The device of claim 1, further comprising means for moving said engaging members in said at least three directions.

12. The device of claim 1, wherein at least one elongate member is axially translatable in a substantially up and down direction relative to the base member.

* * * * *